(12) United States Patent
Kwak et al.

(10) Patent No.: US 12,180,144 B2
(45) Date of Patent: Dec. 31, 2024

(54) DIAMINE COMPOUND, POLYIMIDE PRECURSOR AND POLYIMIDE PREPARED BY USING THE SAME, COMPOSITION FOR FORMING POLYIMIDE FILM AND POLYIMIDE FILM PREPARED BY USING THE SAME, AND USES THEREOF

(71) Applicants: SK Innovation Co., Ltd., Seoul (KR); SK ie technology Co., Ltd., Seoul (KR)

(72) Inventors: Hyo Shin Kwak, Daejeon (KR); Hye Ri Kim, Daejeon (KR); Jin Hyung Park, Daejeon (KR); Hyun Kyu Cho, Daejeon (KR)

(73) Assignees: SK Innovation Co., Ltd., Seoul (KR); SK ie technology Co., Ltd., Seoul (KR)

( * ) Notice: Subject to any disclaimer, the term of this patent is extended or adjusted under 35 U.S.C. 154(b) by 172 days.

(21) Appl. No.: 17/967,096

(22) Filed: Oct. 17, 2022

(65) Prior Publication Data
US 2023/0119106 A1   Apr. 20, 2023

(30) Foreign Application Priority Data
Oct. 18, 2021   (KR) ........................ 10-2021-0138667

(51) Int. Cl.
  C07C 323/42   (2006.01)
  C08G 73/10   (2006.01)
  C08J 5/18   (2006.01)

(52) U.S. Cl.
  CPC ............ *C07C 323/42* (2013.01); *C08G 73/10* (2013.01); *C08J 5/18* (2013.01)

(58) Field of Classification Search
  None
  See application file for complete search history.

(56) References Cited

FOREIGN PATENT DOCUMENTS

EP   3381906 A1   10/2018
JP   2006154803 A   6/2006

*Primary Examiner* — Sudhakar Katakam
*Assistant Examiner* — Jennifer C Sawyer
(74) *Attorney, Agent, or Firm* — The Webb Law Firm

(57) ABSTRACT

An embodiment relates to a diamine compound, a polymer including a structural unit derived therefrom, a composition for forming a polyimide film including the polymer, and a polyimide film prepared by using the composition. Specifically, the diamine compound according to an embodiment may be very usefully used as a monomer for preparing a polyimide film that is colorless and has an improved mechanical strength.

5 Claims, No Drawings

DIAMINE COMPOUND, POLYIMIDE PRECURSOR AND POLYIMIDE PREPARED BY USING THE SAME, COMPOSITION FOR FORMING POLYIMIDE FILM AND POLYIMIDE FILM PREPARED BY USING THE SAME, AND USES THEREOF

CROSS-REFERENCE TO RELATED APPLICATION

This application claims priority to Korean Patent Application No. 10-2021-0138667, filed Oct. 18, 2021, the disclosure of which is hereby incorporated by reference in its entirety.

BACKGROUND OF THE INVENTION

Field of the Invention

The following disclosure relates to a novel diamine compound, and a polyimide precursor and a polyimide prepared by using the same.

In addition, the following disclosure relates to a composition for forming a polyimide film including the polyimide precursor and the polyimide, a polyimide film, and uses thereof.

Description of Related Art

Polyimide (PI) has attracted attention as a material that has high heat resistance and is lightweight and flexible. The polyimide is a polymer material that is easily synthesized, may prepare a thin film, and has excellent physical properties, and is a material that has been prominent in various industrial fields.

In particular, recently, as weight reduction, slimming, and flexibility of display devices have become important, research for replacing glass substrates, cover glasses, and the like, that have been widely used in existing displays with the polyimide has been actively conducted. Since the polyimide should secure excellent optical properties and have improved mechanical properties in order to be applied to next-generation display devices, required performance of the polyimide for display devices have become gradually high.

To this end, research for improving mechanical properties by combining a monomer having strong straightness and rigidity with a transparent polyimide (CPI) or introducing an amide group into the transparent polyimide (CPI) have been conducted. However, there is a trade-off relationship between the optical properties and the mechanical properties of the polyimide, and such an attempt has a limitation that the optical properties of the polyimide are deteriorated even though the mechanical properties of the polyimide are improved. In addition, there is a problem that solution handling properties of the polyimide are reduced, such that there is a limitation that a level of difficulty of a process increases or it is impossible to obtain a resin.

Accordingly, the development of a polyimide of which an application range may be expanded by implementing improved mechanical properties, particularly, an excellent modulus while having colorless performance has been demanded.

SUMMARY OF THE INVENTION

An embodiment is directed to providing a diamine compound having a novel structure, which is a monomer capable of preparing a polyimide film capable of simultaneously implementing excellent mechanical properties and optical properties, and a method for preparing the same.

In addition, an embodiment is directed to providing a polyimide precursor and a polyimide including a structural unit derived from the novel diamine compound.

In addition, an embodiment is directed to providing a composition for forming a polyimide film including the polyimide precursor and/or the polyimide.

In addition, an embodiment is directed to providing a polyimide film that has a high strength and is colorless, prepared by using the composition for forming a polyimide film.

In addition, an embodiment is directed to providing a multilayer structure and a display device including the polyimide film.

In one general aspect, a diamine compound is represented by the following Formula 1:

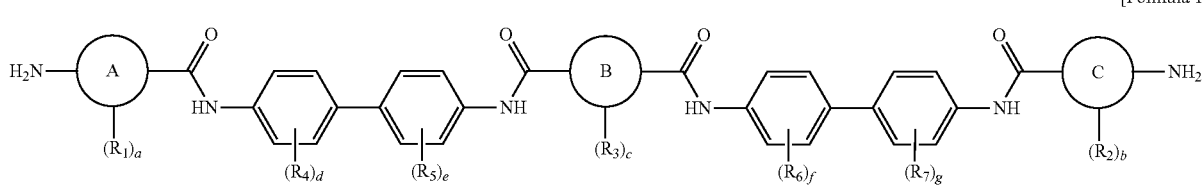

[Formula 1]

wherein rings A to C are each independently (C6-C20) aromatic rings;

$R_1$ to $R_3$ are each independently (C1-C10)alkyl, (C6-C20)aryl, (C3-C10)cycloalkyl, halo(C1-C10)alkyl, (C1-C10)alkylcarbonyl, (C1-C10)alkoxycarbonyl, (C6-C20)arylcarbonyl, —$SiR^aR^bR^c$, —$NR^dR^e$, —COOH, nitro, cyano, or halogen;

$R_4$ to $R_7$ are each independently (C1-C10)alkyl, (C6-C20)aryl, (C3-C10)cycloalkyl, halo(C1-C10)alkyl, (C1-C10)alkylcarbonyl, (C1-C10)alkoxycarbonyl, (C6-C20)arylcarbonyl, (C1-C10)alkoxy, —$SiR^aR^bR^c$, —$NR^dR^e$, —COOH, hydroxy, nitro, cyano, or halogen;

at least one of $R_4$ to $R_7$ is halo(C1-C10)alkyl, (C1-C10)alkylcarbonyl, (C1-C10)alkoxycarbonyl, (C6-C20)arylcarbonyl, —$SiR^aR^bR^c$, nitro, or cyano;

$R^a$ is (C1-C10)alkyl;

$R^b$ to $R^e$ are each independently hydrogen, (C1-C10)alkyl, or (C6-C20)aryl;

a to c are each independently an integer of 0 to 4; and d to g are each independently an integer of 1 to 4.

The diamine compound represented by the Formula 1 may be represented by the following Formula 2:

[Formula 2]

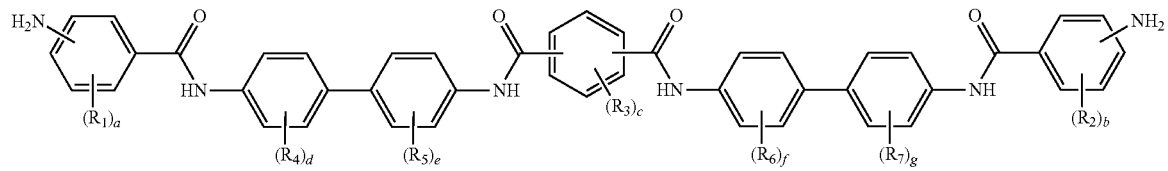

wherein
$R_1$ to $R_3$ are each independently (C1-C7)alkyl, (C6-C12)aryl, (C3-C7)cycloalkyl, halo(C1-C7)alkyl, (C1-C7)alkylcarbonyl, (C6-C12)arylcarbonyl, —SiR$^a$R$^b$R$^c$, —NR$^d$R$^e$, —COOH, nitro, cyano, or halogen;

$R_4$ to $R_7$ are each independently (C1-C7)alkyl, (C6-C12)aryl, (C3-C7)cycloalkyl, halo(C1-C7)alkyl, (C1-C7)alkylcarbonyl, (C1-C7)alkoxycarbonyl, (C6-C12)arylcarbonyl, (C1-C7)alkoxy, —SiR$^a$R$^b$R$^c$, —NR$^d$R$^e$, —COOH, hydroxy, nitro, cyano, or halogen;

at least one of $R_4$ to $R_7$ is halo(C1-C7)alkyl, (C1-C7)alkylcarbonyl, (C1-C7)alkoxycarbonyl, (C6-C12)arylcarbonyl, —SiR$^a$R$^b$R$^c$, nitro, or cyano;

$R^a$ is (C1-C7)alkyl;

$R^b$ to $R^e$ are each independently hydrogen, (C1-C7)alkyl, or (C6-C12)aryl;

a to c are each independently an integer of 0 to 3; and d to g are each independently an integer of 1 to 3.

The diamine compound represented by the Formula 1 may be represented by the following Formula 3:

[Formula 3]

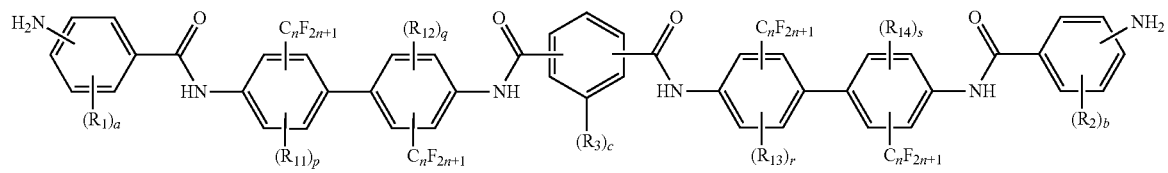

wherein
$R_1$ to $R_3$ and $R_{11}$ to $R_{14}$ are each independently halo(C1-C5)alkyl or halogen;
a to c are each independently 0 or 1;
p to s are each independently 0 or 1; and
n is an integer from 1 to 5.

The diamine compound represented by the Formula 1 may be represented by the following Formula 4:

[Formula 4]

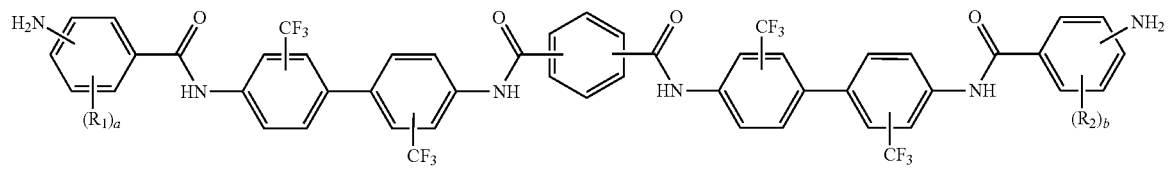

wherein
$R_1$ and $R_2$ are each independently halo(C1-C5)alkyl or halogen; and
a and b are each independently 0 or 1.

The diamine compound represented by the Formula 1 may be selected from the following:

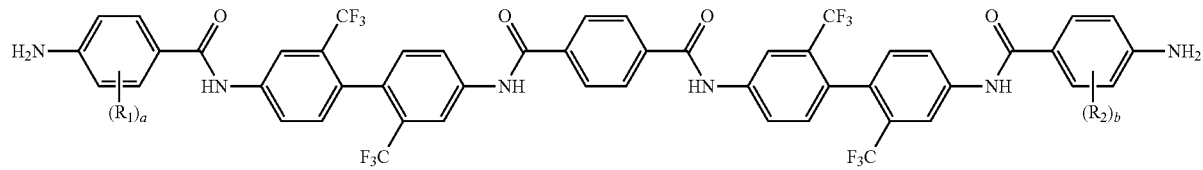

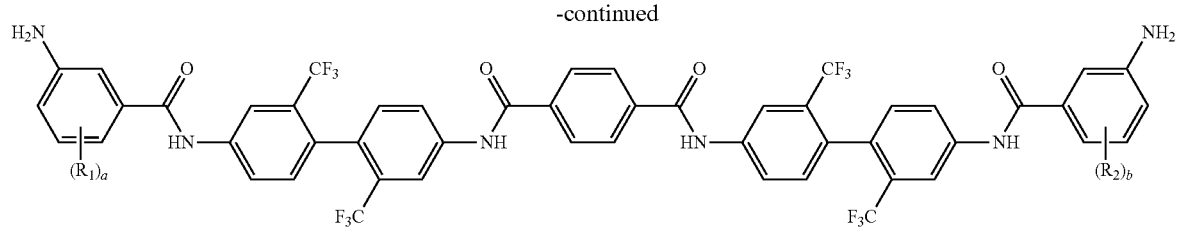

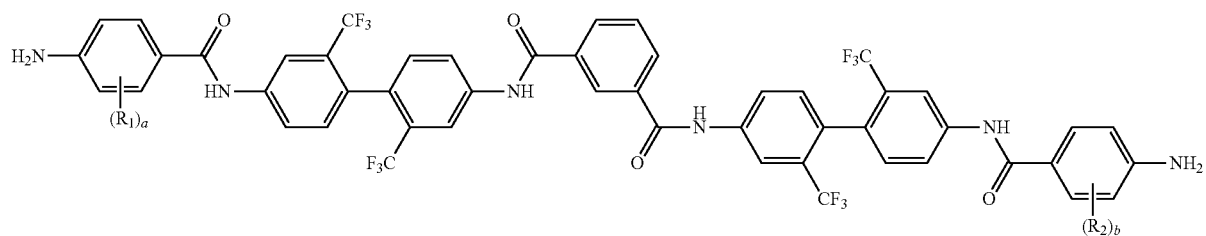

wherein $R_1$ and $R_2$ are each independently fluoro or trifluoromethyl; and a and b are each independently 0 or 1.

In another general aspect, a polyimide precursor includes: a structural unit derived from a diamine compound represented by the following Formula 11 and a structural unit derived from a dianhydride:

[Formula 11]

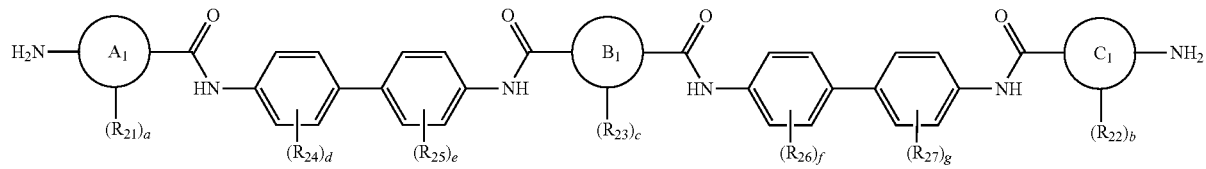

wherein rings $A_1$ to $C_1$ are each independently (C6-C20) aromatic rings;

$R_{21}$ to $R_{27}$ are each independently (C1-C10)alkyl, (C6-C20)aryl, (C3-C10)cycloalkyl, halo(C1-C10)alkyl, (C1-C10)alkylcarbonyl, (C1-C10)alkoxycarbonyl, (C6-C20)arylcarbonyl, (C1-C10)alkoxy, $-SiR^aR^bR^c$, $-NR^dR^e$, $-COOH$, hydroxy, nitro, cyano, or halogen;

$R^a$ is (C1-C10)alkyl;

$R^b$ to $R^e$ are each independently hydrogen, (C1-C10)alkyl, or (C6-C20)aryl;

a to c are each independently an integer of 0 to 4; and d to g are each independently an integer of 1 to 4.

The diamine compound represented by the Formula 11 may be represented by the following Formula 12:

[Formula 12]

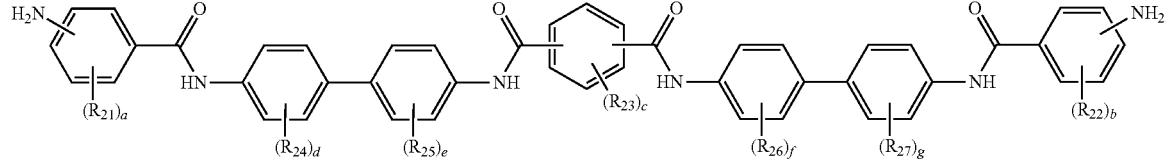

wherein $R_{21}$ to $R_{27}$ are each independently (C1-C7)alkyl, (C6-C12)aryl, (C3-C7)cycloalkyl, halo(C1-C7)alkyl, (C1-C7)alkylcarbonyl, (C1-C7)alkoxycarbonyl, (C6-C12)arylcarbonyl, (C1-C7)alkoxy, —SiR$^a$R$^b$R$^c$, —NR$^d$R$^e$, —COOH, hydroxy, nitro, cyano, or halogen;

$R^a$ is (C1-C7)alkyl;

$R^b$ to $R^e$ are each independently hydrogen, (C1-C7)alkyl, or (C6-C12)aryl;

a to c are each independently an integer of 0 to 3; and d to g are each independently an integer of 1 to 3.

The diamine compound represented by the Formula 11 may be represented by the following Formula 13-1 or 13-2:

[Formula 13-1]

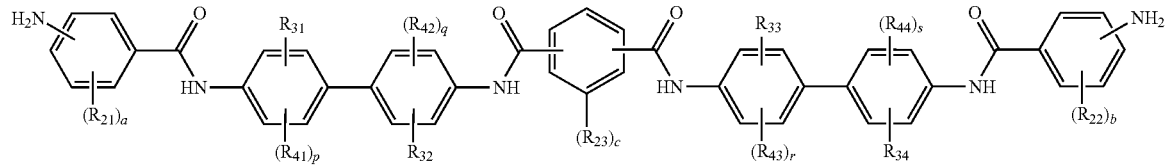

[Formula 13-2]

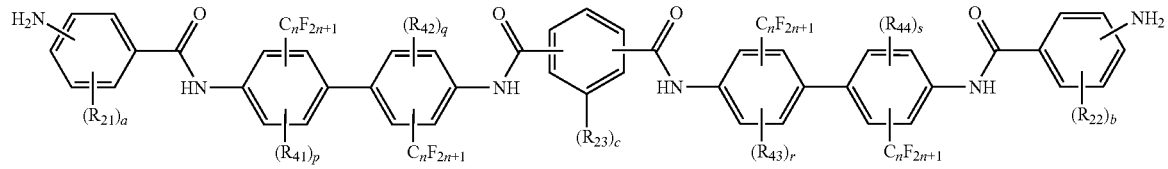

wherein $R_{31}$ to $R_{34}$ are each independently (C1-C5)alkyl;

$R_{21}$ to $R_{23}$ and $R_{41}$ to $R_{44}$ are each independently halo(C1-C5)alkyl or halogen;

a to c are each independently 0 or 1;

p to s are each independently 0 or 1; and n is an integer from 1 to 5.

The diamine compound represented by the Formula 11 may be represented by the following Formula 14-1 or 14-2:

[Formula 14-1]

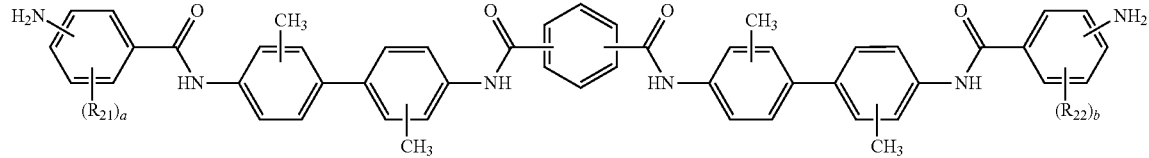

[Formula 14-2]

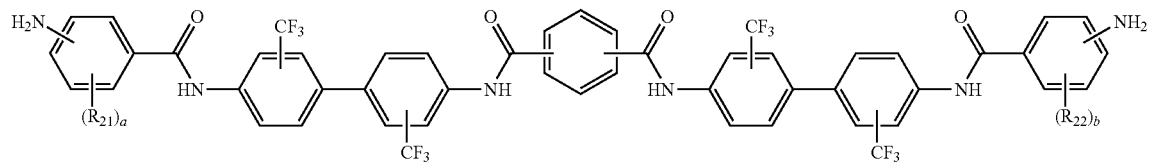

wherein
R$_{21}$ and R$_{22}$ are each independently halo (C1-C5)alkyl or halogen; and
a and b are each independently 0 or 1.

The diamine compound represented by the Formula 11 may be selected from the following structures:

The polyimide precursor may further include a structural unit derived from an aromatic diacid dichloride.

The aromatic diacid dichloride may be any one or two or more selected from the group consisting of terephthaloyl dichloride, isophthaloyl dichloride, 1,1'-biphenyl-4,4'-dicar-

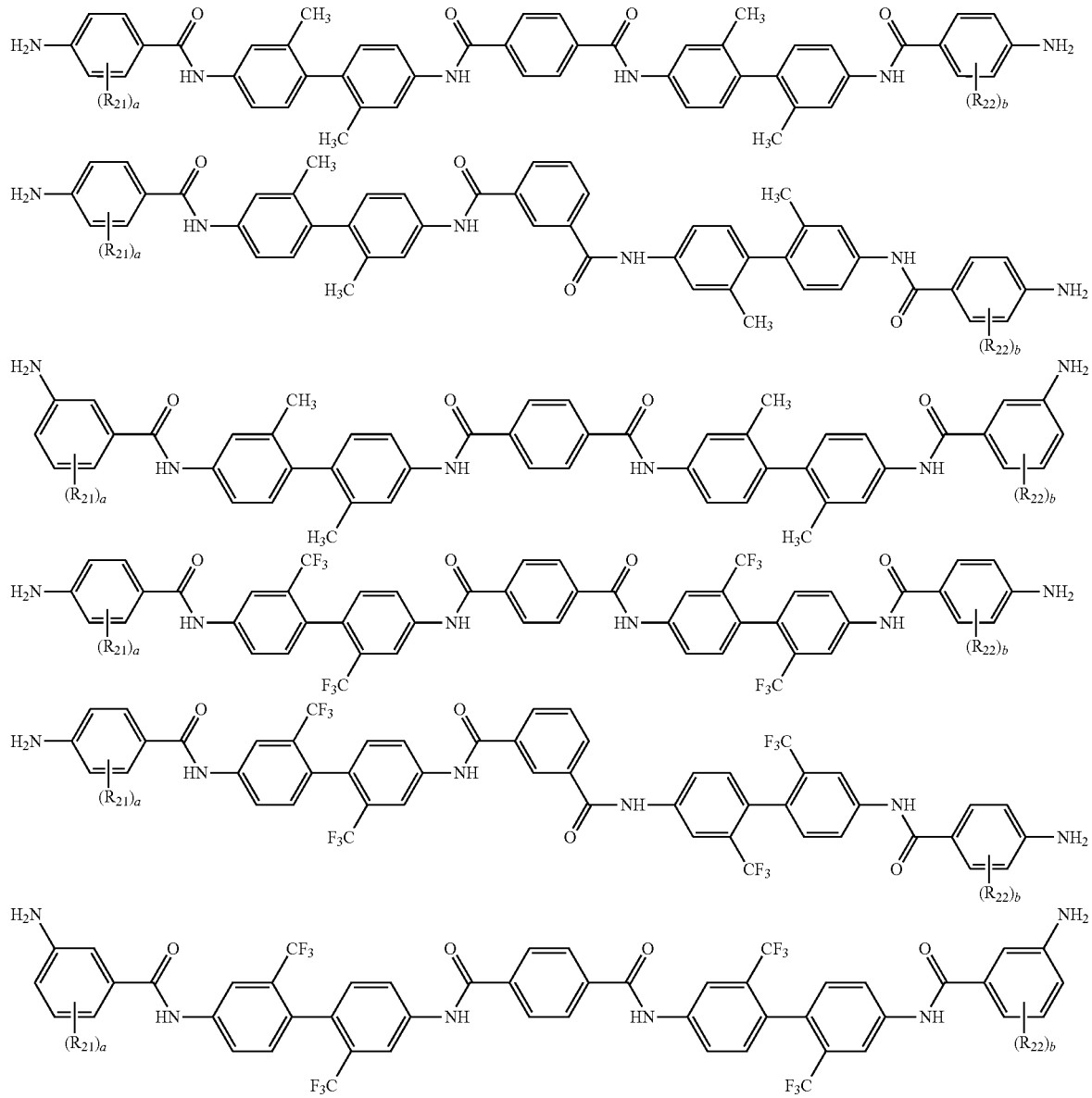

wherein R$_{21}$ and R$_{22}$ are each independently fluoro or trifluoromethyl; and
a and b are each independently 0 or 1.

The polyimide precursor may further include a structural unit derived from an aromatic diamine compound including 2,2'-bis(trifluoromethyl)benzidine.

The dianhydride may be selected from the group consisting of an aromatic dianhydride, an alicyclic dianhydride, or a combination thereof.

The aromatic dianhydride may include 4,4'-(hexafluoroisopropylidene)-diphthalic anhydride, and the alicyclic dianhydride may include 1,2,3,4-cyclobutanetetracarboxylic dianhydride.

bonyl dichloride, 1,4-naphthalenedicarboxylic dichloride, 2,6-naphthalenedicarboxylic dichloride, and 1,5-naphthalenedicarboxylic dichloride.

In still another general aspect, a polyimide is prepared by using the polyimide precursor.

In still another general aspect, a composition for forming a polyimide film includes the polyimide precursor, a polyimide prepared by using the polyimide precursor, or a combination thereof.

In still another general aspect, a polyimide film is formed by the composition for forming a polyimide film.

The polyimide film may have a modulus according to ASTM D882 of 6 GPa or more.

In still another general aspect, a display device includes the polyimide film.

DETAILED DESCRIPTION OF EMBODIMENTS

In the present invention, unless otherwise defined, all technical and scientific terms have the same meanings as the meanings generally understood by those skilled in the art to which the present invention belongs. The terms as used herein are used only for the purpose of effectively describing specific embodiments and are not intended to limit the invention.

Singular forms of the terms as used herein may be intended to include plural forms unless otherwise indicated in the context.

As used herein, the term "include" is an open-ended description having an equivalent meaning to an expression such as "comprise", "contain", "have", or "characterized by", and does not exclude elements, materials, or processes that are not additionally mentioned.

As used herein, the term "A and/or B" may refer to an aspect including A and B at the same time or may refer to an aspect including that selected from A and B.

As used herein, the term "polymer" includes an oligomer and includes a homopolymer and a copolymer, and the copolymer may include an alternating copolymer, a block copolymer, a random copolymer, a branched copolymer, a crosslinked copolymer, or all of them.

As used herein, the term "polyamic acid" refers to a polymer including a structural unit having an amic acid moiety, and the term "polyimide" refers to a polymer including a structural unit having an imide moiety, and may be used as the meaning including polyimide or polyamide-imide.

As used herein, the term "polyimide-based polymer" refers to both of a polyimide and a polyimide precursor (i.e., polyamic acid or polyamic acid ester).

As used herein, the term "CA-CB" means that "the number of carbon atoms is A or more and B or less", and the term "A to B" refers to "A or more to B or less".

As used herein, the term "halogen" may refer to a fluorine (F), chlorine (Cl), bromine (Br) or iodine (I) atom.

As used herein, the term "alkyl" is an organic radical derived from an aliphatic hydrocarbon by the removal of one hydrogen, and may include both straight and branched chain forms. The alkyl may have 1 to 10 carbon atoms, specifically 1 to 7 carbon atoms, and specifically 1 to 5 carbon atoms. Examples of the alkyl include, but are not limited to, methyl, ethyl, propyl, isopropyl, butyl, isobutyl, t-butyl, pentyl, hexyl, ethylhexyl, and the like.

As used herein, the term "alkoxy" is represented by *—O-alkyl, where alkyl is the same as the definition described above.

As used herein, the term "haloalkyl" may mean that at least one hydrogen in the alkyl is substituted with halogen.

As used herein, the term "aryl" is an organic radical derived from an aromatic hydrocarbon by the removal of one hydrogen, includes a single or fused ring system appropriately including 4 to 7, preferably 5 or 6 ring atoms in each ring, and may also include a form in which a plurality of aryls are linked to each other by a single bond. Examples of the aryl include, but are not limited to, phenyl, naphthyl, biphenyl, terphenyl, and the like.

As used herein, the term "arylene" is a divalent functional group derived from arene, and the description of the aryl provided above may be applied to the arylene except that the arylene is a divalent functional group. For example, the arylene may be phenylene, biphenylene, terphenylene, naphthalene, fluorenylene, pyrenylene, phenanthrenylene, perylene, anthracenylene, and the like.

As used herein, the term "alkylcarbonyl" refers to an *—C(=O)alkyl radical, where alkyl is the same as the definition described above. As an example, examples of an alkylcarbonyl radical include, but are not limited to, methylcarbonyl, ethylcarbonyl, isopropylcarbonyl, propylcarbonyl, butylcarbonyl, isobutylcarbonyl, t-butylcarbonyl, and the like.

As used herein, the term "alkoxycarbonyl" refers to an *—C(=O)alkoxy radical, where alkoxy is the same as the definition described above. Examples of the alkoxycarbonyl include, but are not limited to, methoxycarbonyl, ethoxycarbonyl, isopropoxycarbonyl, propoxycarbonyl, butoxycarbonyl, isobutoxycarbonyl, t-butoxycarbonyl, and the like.

As used herein, the term "arylcarbonyl" refers to a *—C(=O)aryl radical, where aryl is the same as the definition described above. Examples of the arylcarbonyl include, but are not limited to, phenylcarbonyl, naphthylcarbonyl, anthrylcarbonyl, and the like.

As used herein, the term "cyano" may refer to —CN, the term "nitro" may refer to —$NO_2$, the term "hydroxy" may refer to —OH, and the term "amine" may refer to —$NH_2$.

In order to apply a polyimide film to a display device, it is necessary to improve inherent yellowness properties of the polyimide film, secure colorless performance of the polyimide film, and improve mechanical properties of the polyimide film. However, when a compound having a rigid structure is used or a polymer in which an amide structure is introduced is prepared as a film in order to improve the mechanical properties of the polyimide film, there is a limitation that optical properties of the polyimide film are deteriorated even though the mechanical properties of the polyimide film are improved. Accordingly, there is a need for a novel diamine compound capable of significantly improving mechanical properties while maintaining colorless properties of a colorless polyimide film.

The novel diamine compound according to an embodiment may improve a mechanical strength of the film by including a plurality of aromatic rings. At the same time, the novel diamine compound according to an embodiment may decrease a charge transfer complex (CTC) effect by having a plurality of amide bonds to decrease π-conjugation. That is, the novel diamine compound according to an embodiment may provide a polyimide film having significantly improved mechanical properties without deterioration of optical properties.

The aromatic ring may include a single ring; a non-fused ring in which two or more aromatic rings are linked to each other by a single bond, a substituted or unsubstituted C1-C5 alkylene group, or O or C(=O); or a combination thereof. Specifically, the aromatic ring may include benzene, biphenyl, or a combination thereof.

As an example, in the novel diamine compound, the aromatic ring may include at least one benzene and at least one biphenyl, the aromatic rings may be linked to each other by an amide group, and specifically, the novel diamine compound may be represented by the following Formula 1:

[Formula 1]

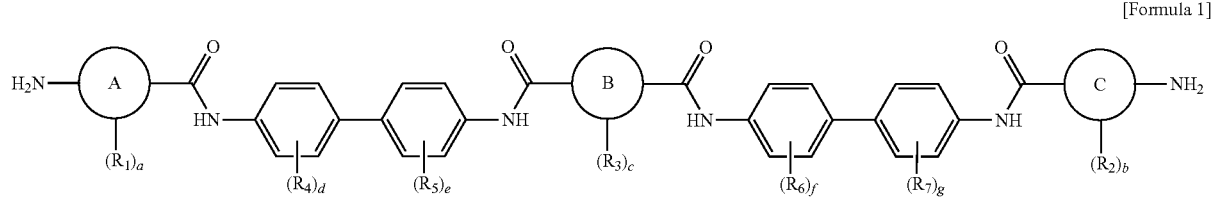

wherein
rings A to C are each independently (C6-C20) aromatic rings;
$R_1$ to $R_3$ are each independently (C1-C10)alkyl, (C6-C20) aryl, (C3-C10)cycloalkyl, halo(C1-C10)alkyl, (C1-C10)alkylcarbonyl, (C1-C10)alkoxycarbonyl, (C6-C20)arylcarbonyl, $-SiR^aR^bR^c$, $-NR^dR^e$, $-COOH$, nitro, cyano, or halogen;
$R_4$ to $R_7$ are each independently (C1-C10)alkyl, (C6-C20) aryl, (C3-C10)cycloalkyl, halo(C1-C10)alkyl, (C1-C10)alkylcarbonyl, (C1-C10)alkoxycarbonyl, (C6-C20)arylcarbonyl, (C1-C10)alkoxy, $-SiR^aR^bR^c$, $-NR^dR^e$, $-COOH$, hydroxy, nitro, cyano, or halogen;
at least one of $R_4$ to $R_7$ is halo(C1-C10)alkyl, (C1-C10) alkylcarbonyl, (C1-C10)alkoxycarbonyl, (C6-C20) arylcarbonyl, $-SiR^aR^bR^c$, nitro, or cyano;
$R^a$ is (C1-C10)alkyl;
$R^b$ to $R^e$ are each independently hydrogen, (C1-C10)alkyl, or (C6-C20)aryl;
a to c are each independently an integer of 0 to 4; and
d to g are each independently an integer of 1 to 4.

In an embodiment, when a to c in the Formula 1 are an integer of 2 or more, $R_1$, $R_2$, and $R_3$ may be the same as or different from each other, and when d to g in the Formula 1 are an integer of 2 or more, $R_4$, $R_5$, $R_6$, and $R_7$ may be the same as or different from each other.

The rings A to C according to an embodiment may be, for example, benzene or naphthalene, and specifically, the diamine compound may be represented by the following Formula 2:

[Formula 2]

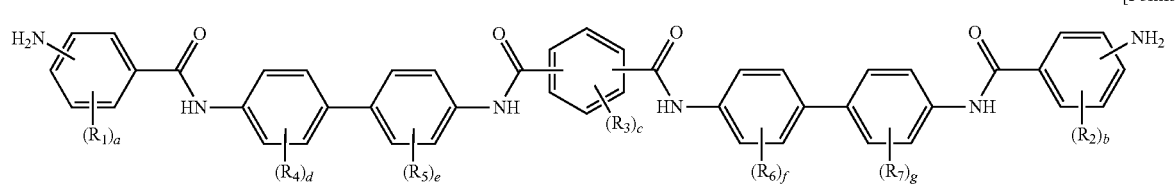

wherein
$R_1$ to $R_3$ are each independently (C1-C7)alkyl, (C6-C12) aryl, (C3-C7)cycloalkyl, halo(C1-C7)alkyl, (C1-C7)alkylcarbonyl, (C6-C12)arylcarbonyl, $-SiR^aR^bR^c$, $-NR^dR^e$, $-COOH$, nitro, cyano, or halogen;
$R_4$ to $R_7$ are each independently (C1-C7)alkyl, (C6-C12) aryl, (C3-C7)cycloalkyl, halo(C1-C7)alkyl, (C1-C7)alkylcarbonyl, (C1-C7)alkoxycarbonyl, (C6-C12)aryl-carbonyl, (C1-C7)alkoxy, $-SiR^aR^bR^c$, $-NR^dR^e$, $-COOH$, hydroxy, nitro, cyano, or halogen;
at least one of $R_4$ to $R_7$ is halo(C1-C7)alkyl, (C1-C7) alkylcarbonyl, (C1-C7)alkoxycarbonyl, (C6-C12)aryl-carbonyl, $-SiR^aR^bR^c$, nitro, or cyano;
$R^a$ is (C1-C7)alkyl;
$R^b$ to $R^e$ are each independently hydrogen, (C1-C7)alkyl, or (C6-C12)aryl;
a to c are each independently an integer of 0 to 3; and
d to g are each independently an integer of 1 to 3.

In an embodiment, when a to c in the Formula 2 are an integer of 2 or more, $R_1$, $R_2$, and $R_3$ may be the same as or different from each other, and when d to g in the Formula 2 are an integer of 2 or more, $R_4$, $R_5$, $R_6$, and $R_7$ may be the same as or different from each other.

In an embodiment, in the Formulas 1 and 2, at least one of $R_4$ to $R_7$ may be halo(C1-C7)alkyl, for example, at least one of $R_4$ may be halo(C1-C7)alkyl, at least one of $R_5$ may be halo(C1-C7)alkyl, at least one of $R_6$ may be halo(C1-C7)alkyl, and at least one of $R_7$ may be halo(C1-C7)alkyl. Accordingly, it is possible to more effectively improve a phenomenon in which the optical properties of the film are deteriorated. Here, halo(C1-C7)alkyl may be perfluoro(C1-C7)alkyl, and more specifically $-CF_3$, $-C_2F_5$, $-C_3F_7$, $-C_4F_9$, or $-C_5F_{11}$, but is not limited thereto.

In addition, in the Formulas 1 and 2, a to c may be each independently an integer of 0 or 1, and d to g may be each independently an integer of 1 or 2.

By introducing a fluoro-substituted alkyl group capable of decreasing the charge transfer complex (CTC) effect into the biphenyl group, the mechanical properties of the film may be improved, and the phenomenon in which the optical properties of the film are deteriorated may be more effectively improved. Here, the fluoro-substituted alkyl group may be the same as described above. More specifically, the diamine compound may be represented by the following Formula 3:

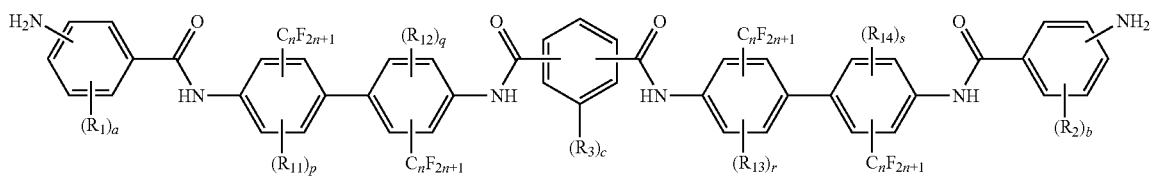

[Formula 3]

wherein
$R_1$ to $R_3$ and $R_{11}$ to $R_{14}$ are each independently halo(C1-C5)alkyl or halogen;
a to c are each independently 0 or 1;
p to s are each independently 0 or 1; and
n is an integer from 1 to 5.

As an example, in the Formula 3, $R_1$ to $R_3$ and $R_{11}$ to $R_{14}$ may be the same as or different from each other, for example, $R_1$ and $R_2$ may be the same as each other, $R_{11}$ to $R_{14}$ may be the same as each other, and, for example, $R_1$ and $R_2$ and $R_{11}$ to $R_{14}$ may be the same as or different from each other.

As an example, n may be an integer of 1 to 3, and specifically 1 or 2.

More specifically, the diamine compound may be represented by the following Formula 4:

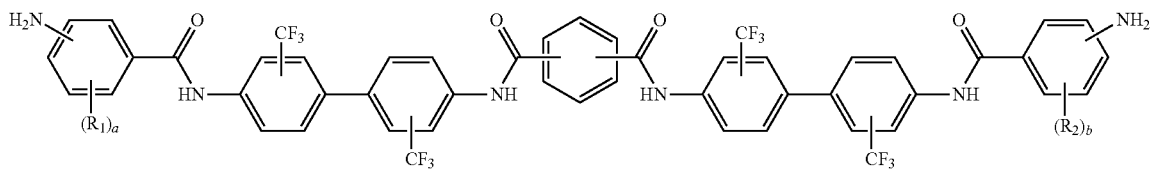

[Formula 4]

wherein
$R_1$ and $R_2$ are each independently halo(C1-C5)alkyl or halogen; and
a and b are each independently 0 or 1.

More specifically, the fluoro-substituted alkyl group ($CF_3$) may be substituted at an ortho position of the biphenyl group. Without wishing to be bound by a particular theory, the fluoro-substituted alkyl group may be substituted at the ortho position of the biphenyl group to induce a twisted structure of two aryl groups in the biphenyl and decrease a packing density and a CTC effect in a polyimide structure or between chains due to a steric hindrance effect. Accordingly, the optical properties of the polyimide film, for example, a yellowness and a haze may be further improved.

The diamine compound according to an embodiment may be, for example, selected from the following, but is not limited thereto:

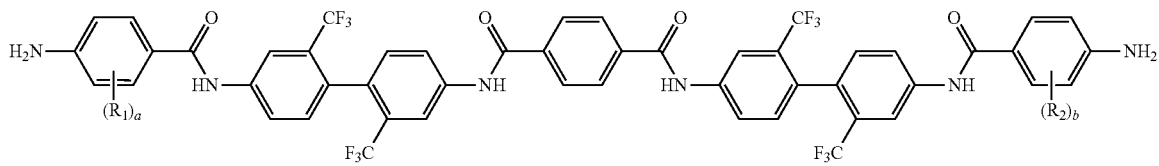

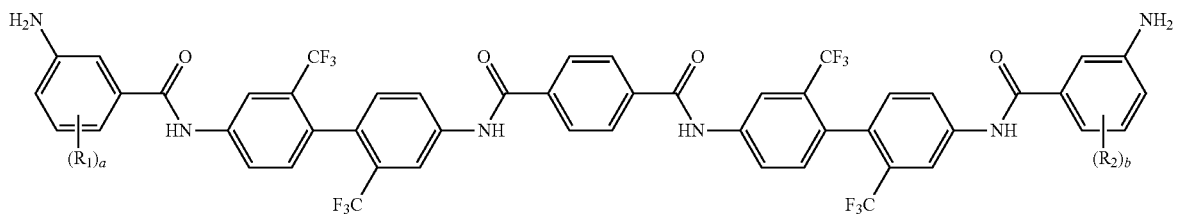

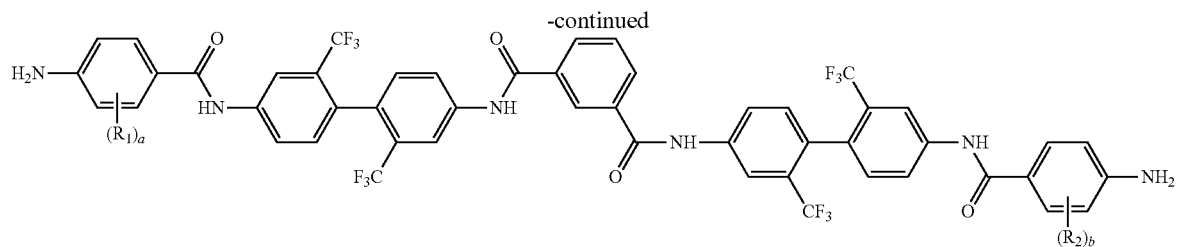
wherein $R_1$ and $R_2$ are each independently fluoro or trifluoromethyl; and
a and b are each independently 0 or 1.
More specifically, the diamine compound may be selected from the following structures, but is not limited thereto.
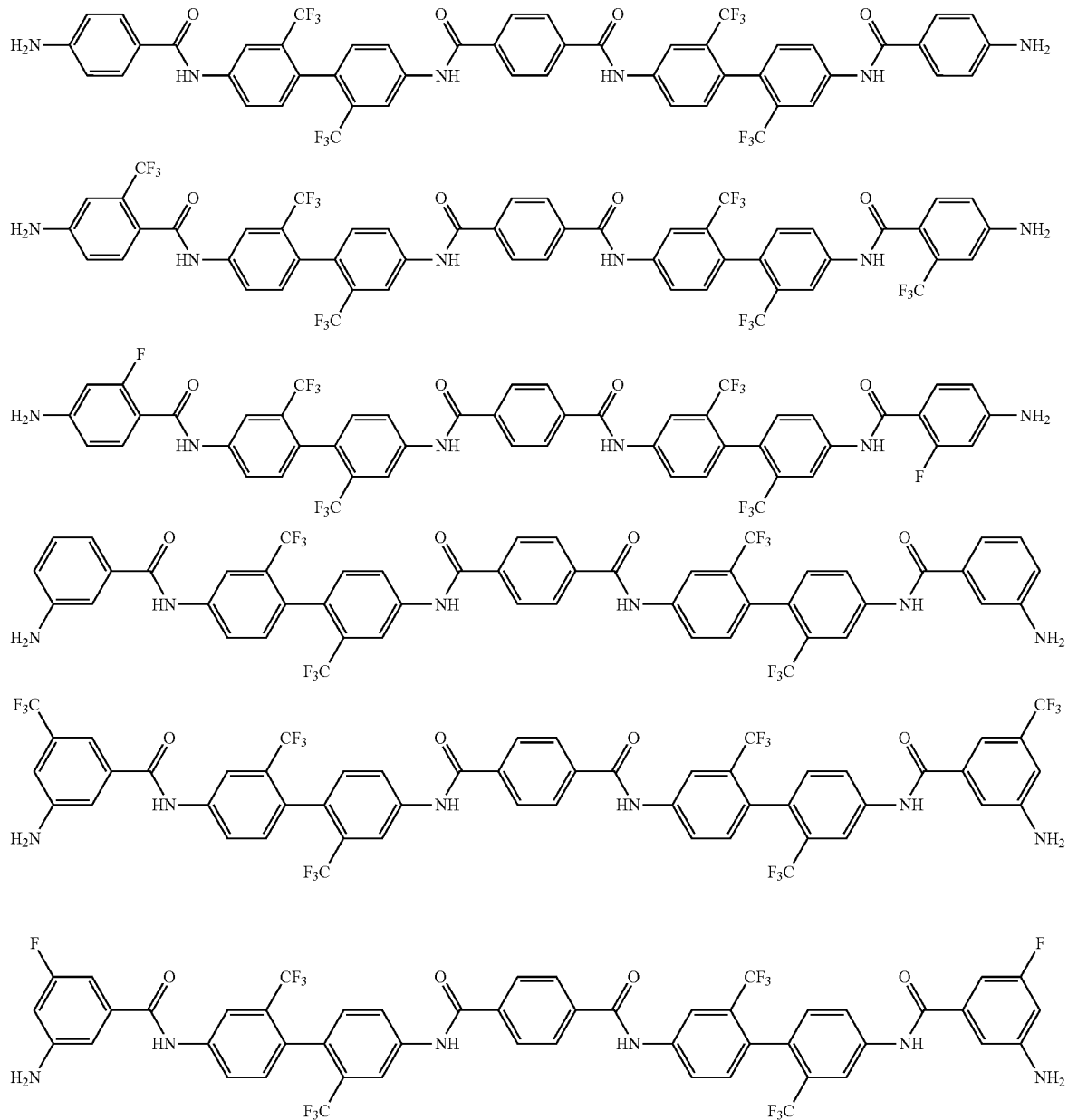

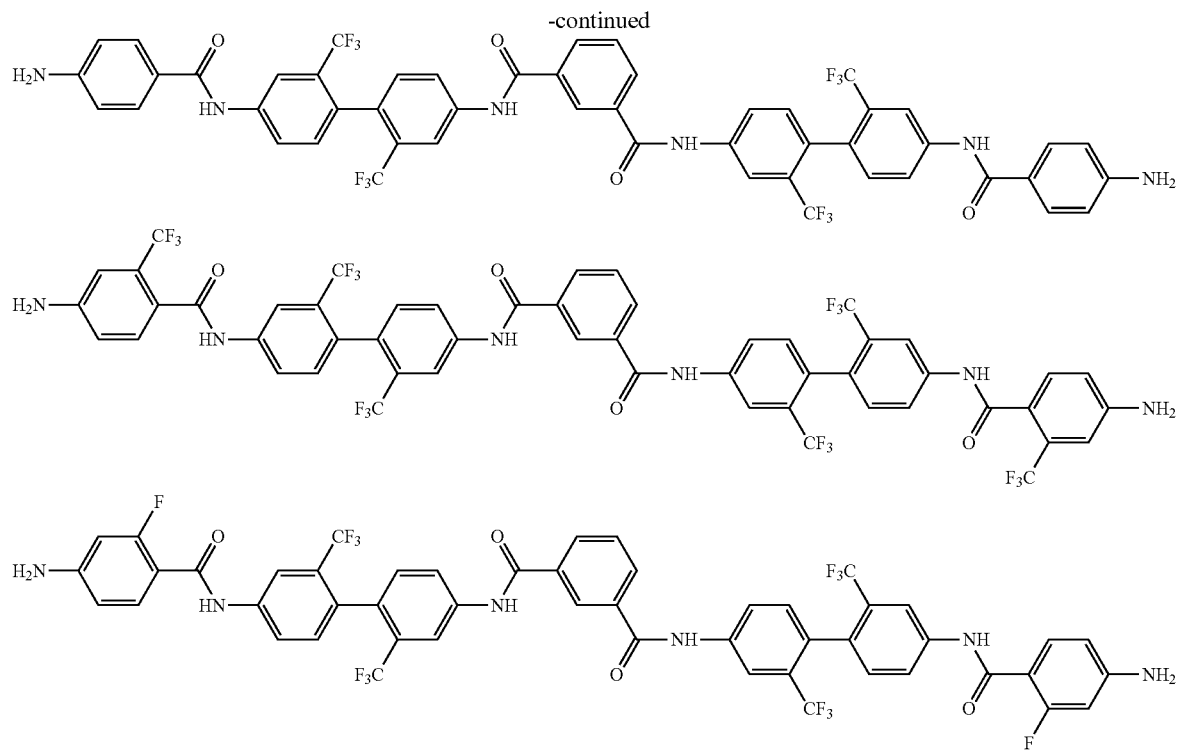

In addition, an embodiment provides a method for preparing the diamine compound.

The method for preparing the diamine compound according to an embodiment includes: a step of preparing a dinitro compound of Formula A by sequentially reacting a compound of Formula C with compounds of Formula B-1 and Formula B-2; and a step of preparing a diamine compound represented by the following Formula 1 by reducing the dinitro compound of Formula A under a reduction catalyst:

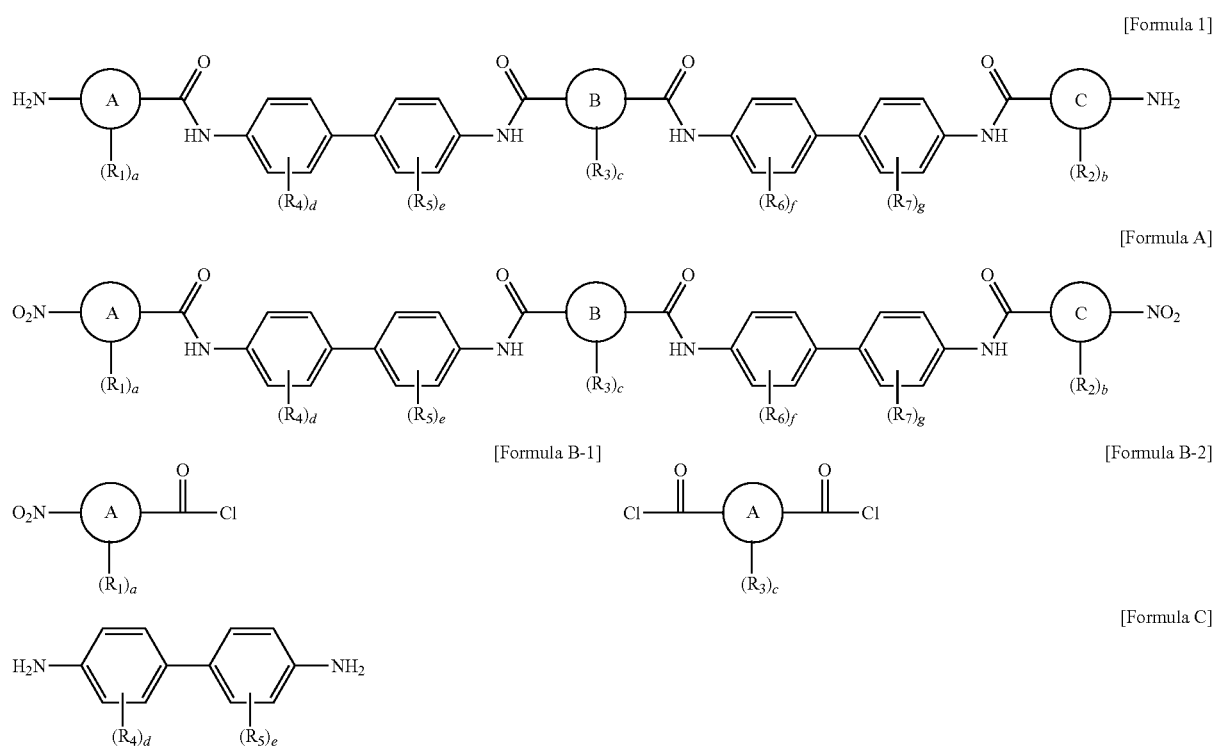

wherein $R_1$ to $R_7$, rings A to C, and a to g are the same as those defined in the Formula 1.

The reduction catalyst according to an embodiment may be selected from the group consisting of Zn, Cu, Ag, Au, Cd, Hg, Fe, $K_4[Fe(CN)_6]$, $NaBH_4$, or a combination thereof. In addition, the reduction catalyst may further include a cocatalyst selected from the group consisting of $NH_4Cl$, $H_2CO_3$, $H_3PO_4$, HCl, $CH_3COOH$, or a combination thereof, and specifically, may be obtained by using Fe and $NH_4Cl$ together.

In an embodiment, the reduction reaction may be performed at 40 to 80° C. for 1 to 10 hours, and specifically at 50 to 70° C. for 4 to 8 hours.

In addition, an embodiment provides a composition for forming a polyimide-based polymer including a novel diamine compound represented by the following Formula 11:

[Formula 11]

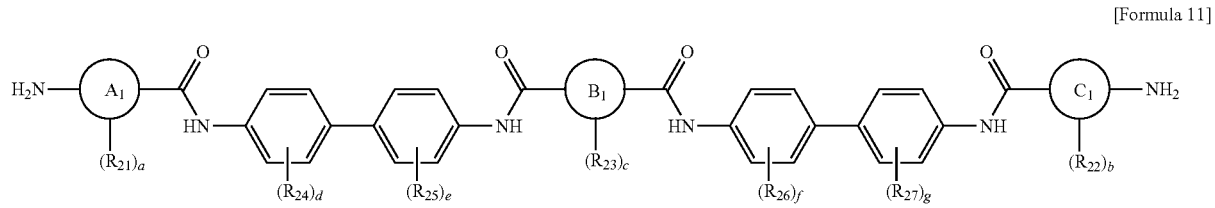

wherein rings $A_1$ to $C_1$ are each independently (C6-C20) aromatic rings;

$R_{21}$ to $R_{27}$ are each independently (C1-C10)alkyl, (C6-C20)aryl, (C3-C10)cycloalkyl, halo(C1-C10)alkyl, (C1-C10)alkylcarbonyl, (C1-C10)alkoxycarbonyl, (C6-C20)arylcarbonyl, (C1-C10)alkoxy, —$SiR^aR^bR^c$, —$NR^dR^e$, —COOH, hydroxy, nitro, cyano, or halogen;

$R^a$ is (C1-C10)alkyl;

$R^b$ to $R^e$ are each independently hydrogen, (C1-C10)alkyl, or (C6-C20)aryl;

a to c are each independently an integer of 0 to 4; and d to g are each independently an integer of 1 to 4.

In an embodiment, when a to c in the Formula 11 are an integer of 2 or more, $R_{21}$, $R_{22}$, and $R_{23}$ may be the same as or different from each other, and when d to g in the Formula 11 are an integer of 2 or more, $R_{24}$, $R_{25}$, $R_{26}$, and $R_{27}$ may be the same as or different from each other.

Specifically, the diamine compound according to an embodiment may be reacted with a dianhydride to synthesize a polyimide precursor (i.e., polyamic acid or polyamic acid ester), and a polyimide may be synthesized through imidization of the polyimide precursor.

That is, the diamine compound according to an embodiment may be applied as a monomer for synthesizing a polyimide-based polymer. In this case, the polyimide-based polymer refers to both of the polyimide and the polyimide precursor (i.e., polyamic acid or polyamic acid ester).

In addition, an embodiment provides a polyimide precursor prepared by using the diamine compound represented by the following Formula 11 as a monomer:

[Formula 11]

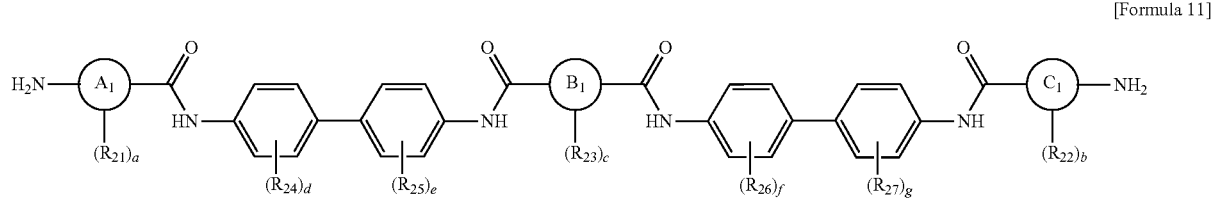

wherein $R_{21}$ to $R_{27}$, rings $A_1$ to $C_1$, and a to g are the same as those defined in the Formula 11.

The polyimide precursor according to an embodiment may include a structural unit derived from the diamine compound of the Formula 11 and a structural unit derived from a dianhydride. More specifically, the polyimide precursor according to an embodiment may include a repeating unit in which a bond between a nitrogen atom of an amino group and a carbon atom of an anhydride group is formed by a reaction between a terminal amino group (—$NH_2$) of the diamine compound and a terminal anhydride group (—OC—O—CO—) of a dianhydride compound.

Since the diamine compound according to an embodiment has the above-described structural feature, for example, a biphenyl group structure and an amide bond, it is possible to prepare a polyimide film having significantly improved mechanical properties, for example, modulus while maintaining excellent optical properties by applying the diamine compound as a monomer.

The rings $A_1$ to $C_1$ according to an embodiment may be, for example, benzene or naphthalene, and specifically, the diamine compound may be represented by the following Formula 12:

[Formula 12]

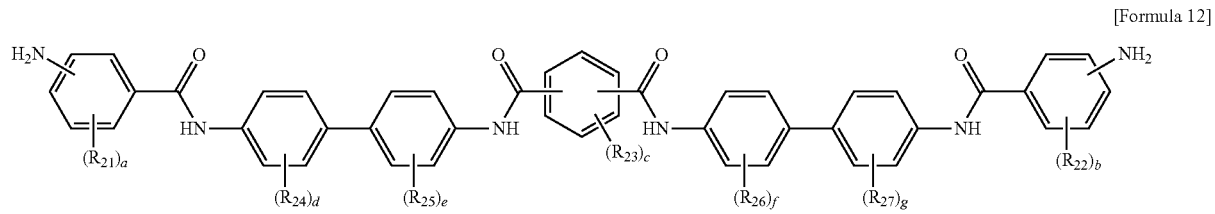

wherein
$R_{21}$ to $R_{27}$ are each independently (C1-C7)alkyl, (C6-C12)aryl, (C3-C7)cycloalkyl, halo(C1-C7)alkyl, (C1-C7)alkylcarbonyl, (C1-C7)alkoxycarbonyl, (C6-C12)arylcarbonyl, (C1-C7)alkoxy, —$SiR^aR^bR^c$, —$NR^dR^e$, —COOH, hydroxy, nitro, cyano, or halogen;
$R^a$ is (C1-C7)alkyl;
$R^b$ to $R^e$ are each independently hydrogen, (C1-C7)alkyl, or (C6-C12)aryl;
a to c are each independently an integer of 0 to 3; and
d to g are each independently an integer of 1 to 3.

In an embodiment, when a to c in the Formula 12 are an integer of 2 or more, $R_{21}$, $R_{22}$, and $R_{23}$ may be the same as or different from each other, and when d to g in the Formula 12 are an integer of 2 or more, $R_{24}$, $R_{25}$, $R_{26}$, and $R_{27}$ may be the same as or different from each other.

In an embodiment, at least one of $R_{24}$ to $R_{27}$ in the Formulas 11 and 12 may be (C1-C7)alkyl, halo(C1-C7)alkyl, or halogen, specifically (C1-C7)alkyl, perfluoro(C1-C7)alkyl or fluoro, and more specifically (C1-C7)alkyl or perfluoro(C1-C7)alkyl. For example, at least one of $R_{24}$ may be (C1-C7)alkyl or perfluoro(C1-C7)alkyl, at least one of $R_{25}$ may be (C1-C7)alkyl or perfluoro(C1-C7)alkyl, at least one of $R_{26}$ may be (C1-C7)alkyl or perfluoro(C1-C7)alkyl, and at least one of $R_{27}$ may be (C1-C7)alkyl or perfluoro(C1-C7)alkyl.

In addition, a to c may be each independently an integer of 0 or 1, and d to g may be each independently an integer of 1 or 2.

More specifically, the diamine compound may be represented by the following Formula 13-1 or 13-2:

[Formula 13-1]

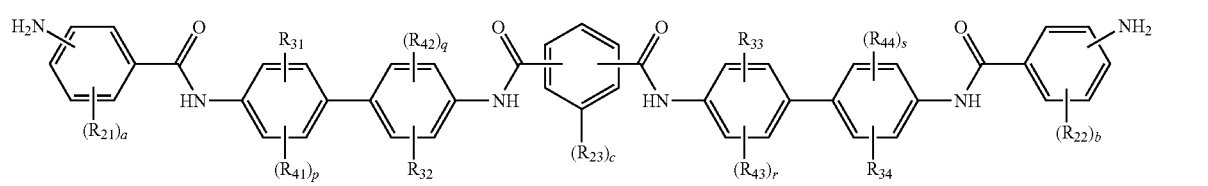

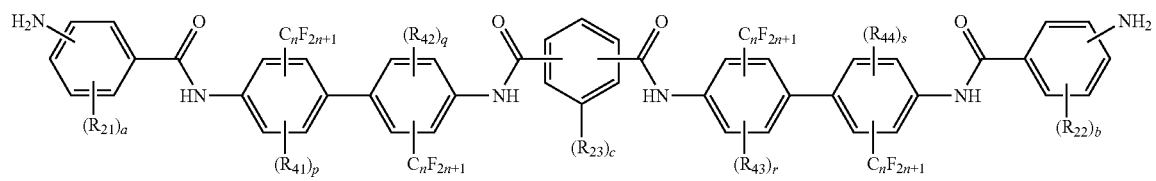

[Formula 13-2]

wherein
R$_{31}$ to R$_{34}$ are each independently (C1-C5)alkyl;
R$_{21}$ to R$_{23}$ and R$_{41}$ to R$_{44}$ are each independently halo(C1-C5)alkyl or halogen;
a to c are each independently 0 or 1;
p to s are each independently 0 or 1; and
n is an integer from 1 to 5.

In an embodiment, n may be an integer of 1 to 3, and specifically 1 or 2.

As an example, R$_{31}$ to R$_{34}$ may be the same as each other, may be (C1-C3)alkyl, and more specifically methyl or ethyl, for example, methyl.

As an example, R$_{21}$ to R$_{23}$ and R$_{41}$ to R$_{44}$ may be the same as or different from each other, for example, R$_{21}$ and R$_{22}$ may be the same as each other, R$_{41}$ to R$_{44}$ may be the same as each other, and, for example, R$_{21}$ and R$_{22}$ and R$_{41}$ to R$_{44}$ may be the same as or different from each other.

More specifically, the diamine compound may be represented by the following Formula 14-1 or 14-2:

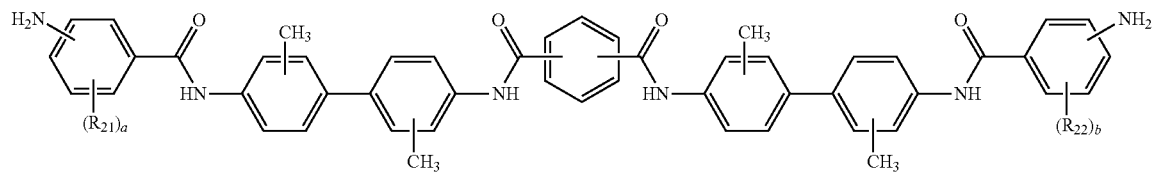

[Formula 14-1]

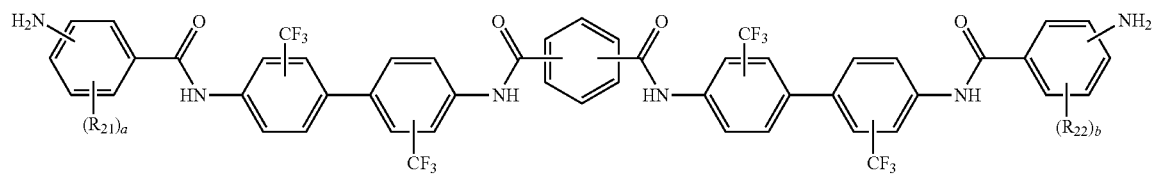

[Formula 14-2]

wherein
R$_{21}$ and R$_{22}$ are each independently halo(C1-C5)alkyl or halogen; and
a and b are each independently 0 or 1.

As an example, R$_{21}$ and R$_{22}$ may be the same as each other, and may be perfluoro(C1-C5)alkyl or fluoro.

More specifically, CF$_3$ and CH$_3$ substituted in the biphenyl group may be substituted at the ortho position of the biphenyl group. Without wishing to be bound by a particular theory, the substituent may be substituted at the ortho position of the biphenyl group to induce a twisted structure of two aryl groups in the biphenyl and decrease a packing density and a CTC effect in a polyimide structure or between chains due to a steric hindrance effect. Accordingly, the optical properties of the polyimide film, for example, a yellowness and a haze may be further improved.

The diamine compound according to an embodiment may be, for example, selected from the following, but is not limited thereto:

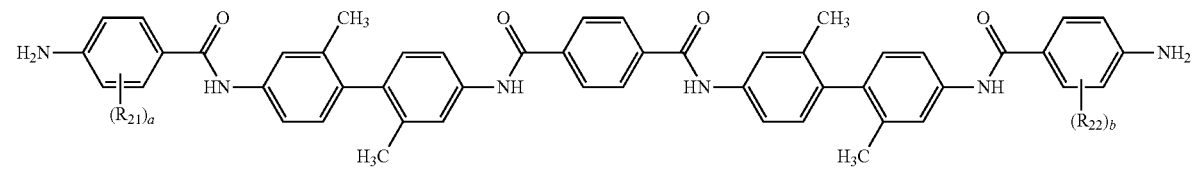

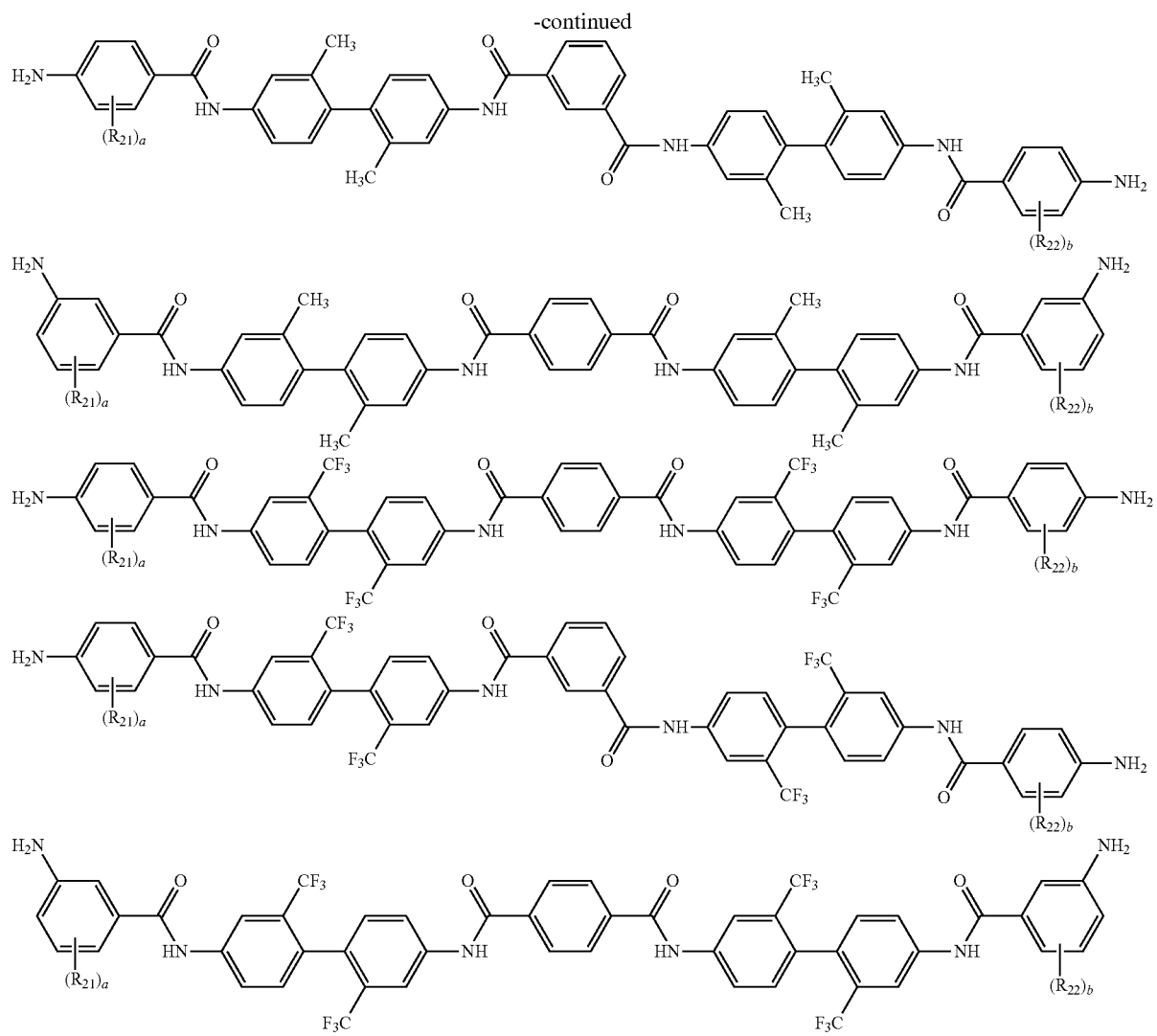
wherein $R_{21}$ and $R_{22}$ are each independently fluoro or trifluoromethyl; and
a and b are each independently 0 or 1.
More specifically, the diamine compound may be selected from the following structures, but is not limited thereto.
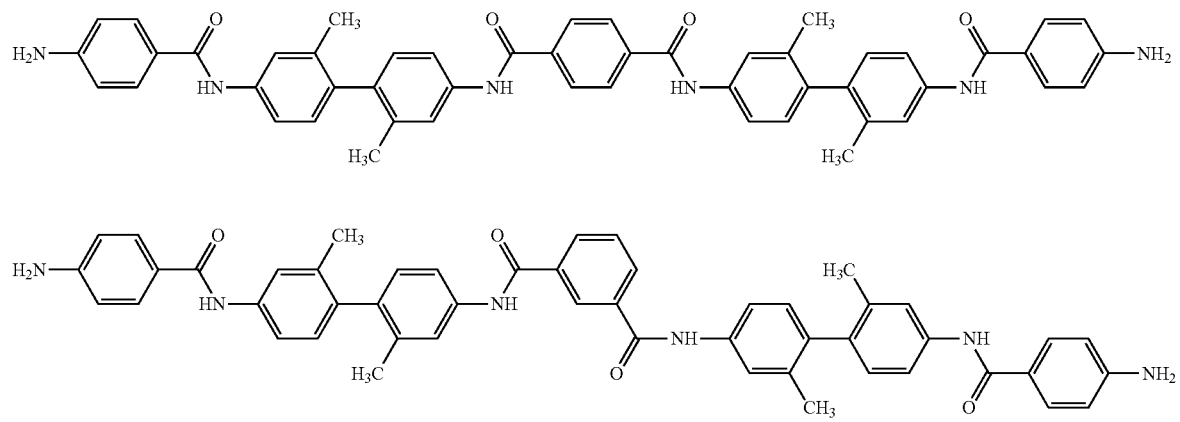

-continued
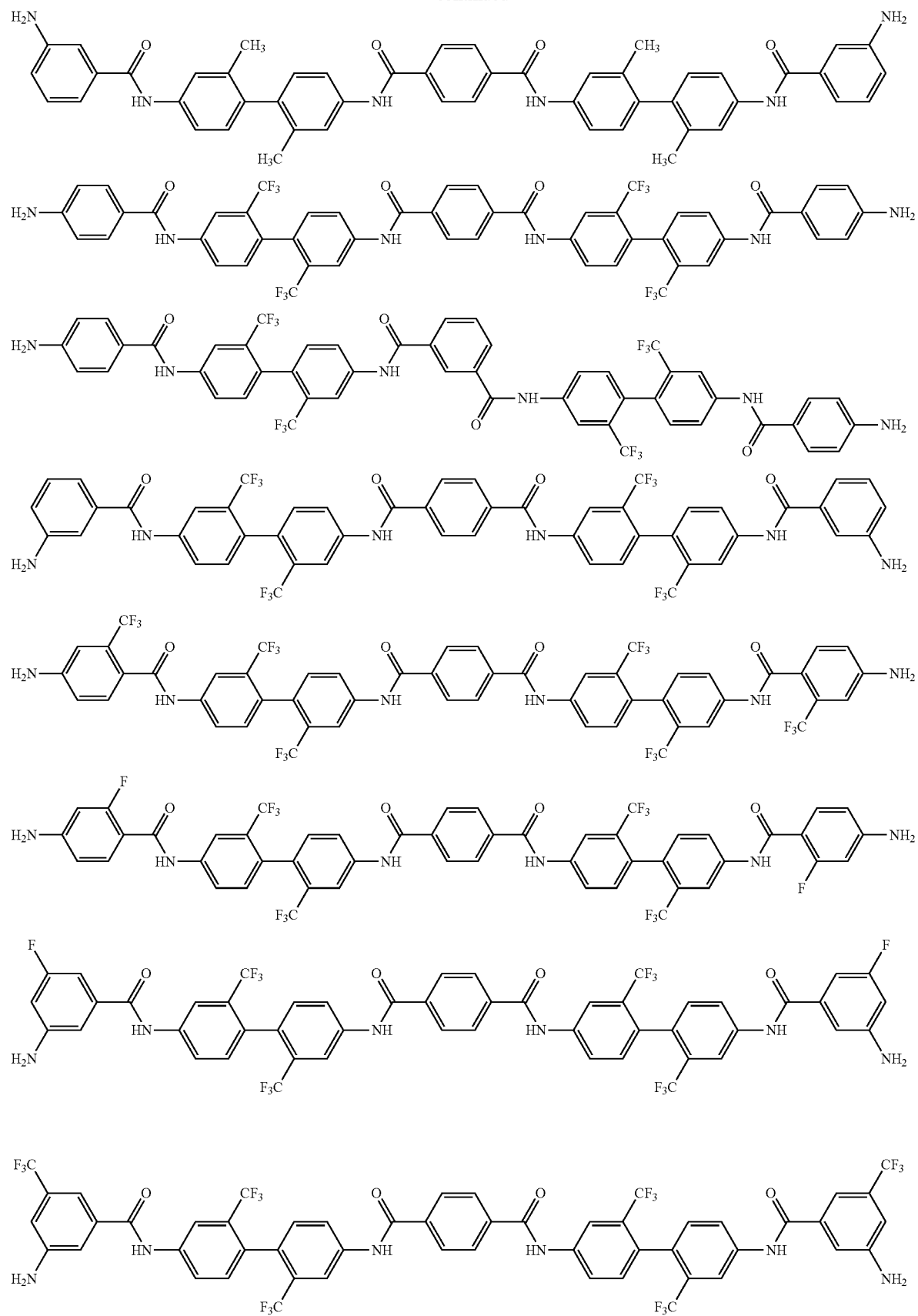

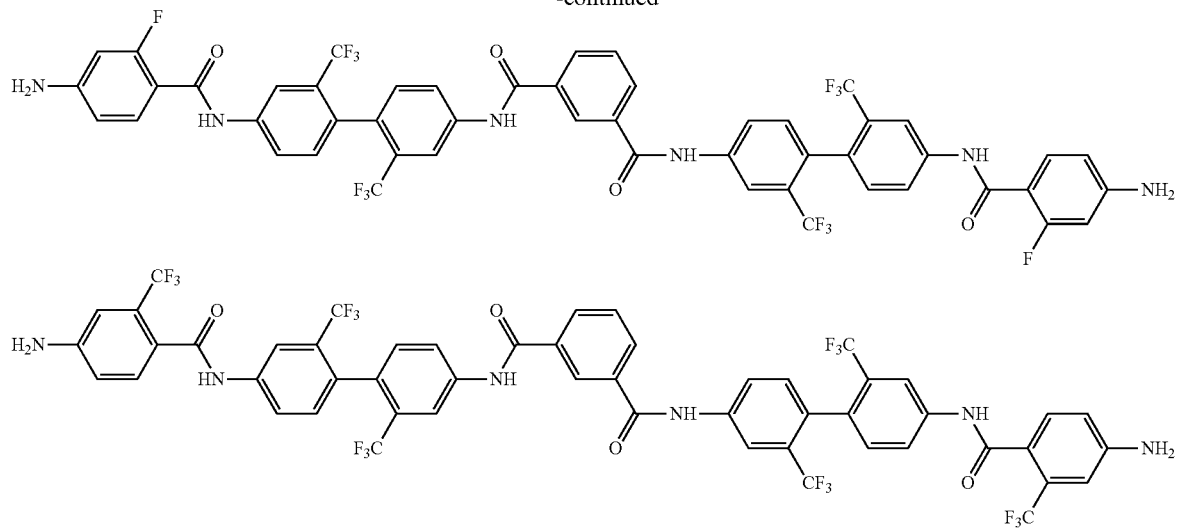

The diamine compound according to an embodiment has the structural feature as described above, the biphenyl group, and the amide bond, and thus, may significantly improve the mechanical properties of the polyimide film without deterioration of the optical properties of the polyimide film. In particular, by introducing a fluoro group and/or a fluoro-substituted alkyl group into the biphenyl group, the phenomenon in which the optical properties of the film are deteriorated may be more effectively improved.

The polyimide precursor according to an embodiment may further include a structural unit derived from a known diamine compound in addition to the structural unit derived from the diamine compound represented by the Formula 11.

The known diamine compound is not particularly limited, but may be, for example, one or two or more selected from the group consisting of PDA (p-phenylenediamine), m-PDA (m-phenylenediamine), 4,4'-ODA (4,4'-oxydianiline), 3,4'-ODA (3,4'-oxydianiline), BAPP (2,2-bis(4-[4-aminophenoxy]-phenyl)propane), TPE-Q (1,4-bis(4-aminophenoxy)benzene), TPE-R (1,3-bis(4-aminophenoxy)benzene), BAPB (4,4'-bis(4-aminophenoxy)biphenyl), BAPS (bis(4-[4-aminophenoxy]phenyl) sulfone), m-BAPS (bis(4-[3-aminophenoxy]phenyl)sulfone), HAB (3,3'-dihydroxy-4,4'-diaminobiphenyl), TB (3,3-dimethylbenzidine), m-TB (2,2'-dimethylbenzidine), TFMB (2,2'-bis(trifluoromethyl)benzidine), 6FAPB (1,4-bis(4-amino-2-trifluoromethylphenoxy)benzene), 6FODA (2,2'-bis(trifluoromethyl)-4,4'-diaminodiphenyl ether), APB (1,3-bis(3-aminophenoxy)benzene), 1,4-ND (1,4-naphthalenediamine), 1,5-ND (1,5-naphthalenediamine), DABA (4,4'-diaminobenzanilide), 6-amino-2-(4-aminophenyl)benzoxazole, and 5-amino-2-(4-aminophenyl)benzoxazole.

Specifically, the diamine compound may be a fluorine-based aromatic diamine compound into which a fluorine substituent is introduced, may be, for example, selected from the group consisting of TFMB (2,2'-bis(trifluoromethyl)benzidine), 6FAPB (1,4-bis(4-amino-2-trifluoromethylphenoxy)benzene), 6FODA (2,2'-bis(trifluoromethyl)-4,4'-diaminodiphenyl ether), or a combination thereof, and more specifically, may be TFMB (2,2-bis(trifluoromethyl)benzidine).

The polyimide precursor further includes the structural unit derived from the fluorine-based aromatic diamine compound as described above, and may thus impart more excellent optical properties to the film.

Specifically, when the diamine compound of the Formula 11 and the known diamine compound are used together, the diamine compound of the Formula 11 and the known diamine compound may be used in a molar ratio of 1:1 to 1:10, specifically a molar ratio of 1:2 to 1:9, and more specifically a molar ratio of 1:4 to 1:9, but are not limited thereto. As the molar ratio is in the above-described range, the mechanical properties of the polyimide film may be further improved.

The dianhydride according to an embodiment may be any compound having an acid dianhydride functional group, but may be, for example, an aromatic dianhydride, an alicyclic dianhydride, or a combination thereof.

The aromatic dianhydride may be, for example, one or two or more selected from the group consisting of BPAF (9,9-bis(3,4-dicarboxyphenyl)fluorene dianhydride), 6FDA (4,4'-(hexafluoroisopropylidene)-diphthalic anhydride), BPDA (biphenyltetracarboxylic dianhydride), ODPA (oxydiphthalic dianhydride), SO2 DPA (sulfonyl diphthalic anhydride), 6 HDBA (isopropylidenediphenoxy)bis (phthalic anhydride)), TDA (4-(2,5-dioxotetrahydrofuran-3-yl)-1,2,3,4-tetrahydronaphthalene-1,2-dicarboxylic dianhydride), PMDA (1,2,4,5-benzene tetracarboxylic dianhydride), and BTDA (benzophenone tetracarboxylic dianhydride), but is not limited thereto.

Specifically, the aromatic dianhydride may be BPAF (9,9-bis(3,4-dicarboxyphenyl)fluorene dianhydride), 6FDA (4,4'-(hexafluoroisopropylidene)-diphthalic anhydride hydride), or a combination thereof, and more specifically, a fluorine-based aromatic dianhydride, for example, 6FDA (4,4'-(hexafluoroisopropylidene)-diphthalic anhydride). By using the fluorine-based aromatic dianhydride as described above, a mechanical strength, in particular, a modulus as well as optical properties of the polyimide film may be more effectively improved.

The alicyclic dianhydride refers to a dianhydride comprising at least one aliphatic ring, wherein the aliphatic ring may be a single ring, a fused ring in which two or more aliphatic rings are fused, a non-fused ring in which two or more aliphatic rings are linked to each other by a single bond, a substituted or unsubstituted (C1-C5)alkylene group, or O or C(=O). For example, the alicyclic dianhydride may be one or two or more selected from the group consisting of CBDA (1,2,3,4-cyclobutanetetracarboxylic dianhydride), DOCDA (5-(2,5-dioxotetrahydrofuryl)-3-methylcyclohexene-1,2-dicarboxylic dianhydride), BTA (bicyclo[2.2.2]oct-7-ene-2,3,5,6-tetracarboxylic dianhydride), BODA (bicyclooctene-2,3,5,6-tetracarboxylic dianhydride), CPDA (1,2,3,4-cyclopentanetetracarboxylic dianhydride), CHDA (1,2,4,5-cyclohexanetetracarboxylic dianhydride), TMDA (1,2,4-tricarboxy-3-methylcarboxycyclopentane dianhydride), TCDA (1,2,3,4-tetracarboxycyclopentane dianhydride), and derivatives thereof, but is not limited thereto. Specifically, the alicyclic dianhydride compound may be CBDA (1,2,3,4-cyclobutanetetracarboxylic dianhydride).

More specifically, the dianhydride according to an embodiment may be a combination of an aromatic dianhydride and an alicyclic dianhydride, for example, a combination of a fluorine-based aromatic dianhydride and an alicyclic dianhydride, for example, a combination of 6FDA (4,4'-(hexafluoroisopropylidene)-diphthalic anhydride) and CBDA (1,2,3,4-cyclobutanetetracarboxylic dianhydride).

In addition, when the polyimide precursor according to an embodiment is prepared, an equivalent ratio between the diamine compound and a mixture of the aromatic dianhydride and the alicyclic dianhydride is not particularly limited, but may be 1:0.9 to 1.1, and specifically 1:0.95 to 1.05. As the equivalent ratio is in the above-described range, physical properties of the film including film forming properties may be further improved.

In addition, the polyimide precursor according to an embodiment may further include a structural unit derived from an aromatic diacid dichloride. The aromatic diacid dichloride forms an amide structure in a polymer chain, and may further improve mechanical properties including a modulus without deteriorating the optical properties of the film.

The aromatic diacid dichloride may be, for example, one or two or more selected from the group consisting of IPC (isophthaloyl dichloride), TPC (terephthaloyl dichloride), BPC (1,1'-biphenyl-4,4'-dicarbonyl dichloride), NPC (1,4-naphthalene dicarboxylic dichloride), NTC (2,6-naphthalene dicarboxylic dichloride), NEC (1,5-naphthalene dicarboxylic dichloride), and the like, but is not limited thereto.

Specifically, TPC (terephthaloyl dichloride) may be used as the aromatic diacid dichloride. As an example, when a content of the terephthaloyl dichloride is 50 mol or more with respect to 100 mol of the aromatic diamine, mechanical properties of the film such as a modulus may be significantly improved. However, an intermolecular density increases, such that a problem that optical properties of the film such as a yellowness and a haze are deteriorated may occur. On the other hand, it was found that it was possible to improve the phenomenon in which the optical properties of the polyimide film were deteriorated by using the diamine compound of the Formula 11 according to an embodiment as the monomer, and it is possible to provide a film that simultaneously satisfies excellent optical and mechanical properties as desired.

When the polyimide precursor according to an embodiment further includes the structural unit derived from the aromatic diacid dichloride, the aromatic diacid dichloride may be used in an amount of 50 mol or more or 55 mol or more, and more specifically 55 to 80 mol, with respect to 100 mol of the diamine compound, but is not limited thereto. When the aromatic diacid dichloride in the above-described range is used, the mechanical properties of the polyimide film may be further improved.

In addition, an embodiment provides a polyimide prepared by using the polyimide precursor.

In addition, an embodiment provides a composition for forming a polyimide film including the polyimide precursor and/or the polyimide.

Specifically, the composition for forming a polyimide film may include a polyimide precursor including a structural unit derived from the diamine compound of the Formula 11, a polyimide, or a mixture thereof; and an organic solvent.

As the composition according to an embodiment includes the above-described polyimide precursor and/or polyimide, and may thus provide a polyimide film having significantly improved mechanical properties. In particular, the composition according to an embodiment may provide a polyimide film having a significantly improved modulus value while maintaining colorless properties.

The organic solvent included in the composition according to an embodiment may be one or a mixture of two or more selected from the group consisting of ketones such as gamma-butyrolactone, 1,3-dimethyl-2-imidazolidinone, methyl ethyl ketone, cyclohexanone, cyclopentanone, and 4-hydroxy-4-methyl-2-pentanone; aromatic hydrocarbons such as toluene, xylene, and tetramethylbenzene; glycol ethers (Cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether and triethylene glycol monoethyl ether; acetates such as ethyl acetate, butyl acetate, ethylene glycol monoethyl ether acetate, ethylene glycol monobutyl ether acetate, diethylene glycol monoethyl ether acetate, and dipropylene glycol monomethyl ether acetate; alcohols such as methanol, ethanol, propanol, ethylene glycol, propylene glycol, and carbitol; amides such as N,N-dimethylpropionamide (DMPA), N,N-diethylpropionamide (DEPA), N,N-dimethylacetamide (DMAc), N,N-diethylacetamide (DEAc), N,N-dimethylformamide (DMF), N,N-diethylformamide (DEF), N-methylpyrrolidone (NMP), N-ethylpyrrolidone (NEP), and N,N-dimethylmethoxyacetamide, and the like, but is not limited thereto.

Specifically, the organic solvent may be one or a mixture of two or more selected from the above-described amides. As an example, the organic solvent may be N,N-dimethylacetamide (DMAc), N,N-diethylacetamide (DEAc), N-ethylpyrrolidone (NEP), N,N-dimethylpropionamide (DMPA), N,N-diethylpropionamide (DEPA), or a combination thereof.

In the composition for forming a polyimide film according to an embodiment, a solid content may be adjusted to an amount in which the composition has an appropriate viscosity, in consideration of applicability and the like in a subsequent film forming process. As an example, in the composition for forming a polyimide film according to an embodiment, a solid content may be 5 to 20 wt %, 10 to 20 wt %, or 10 to 15 wt % based on the total weight of the composition. Here, a solid refers to a polyimide precursor and/or a polyimide.

Specifically, the composition for forming a polyimide film according to an embodiment may have a viscosity of 5,000 to 100,000 cps or 15,000 to 50,000 cps. When the viscosity of the composition for forming a polyimide film is in the above-described range, efficiency of defoaming during processing of the polyimide film may be more excellent to provide an advantage in a process. Accordingly, it is possible to implement a more uniform surface. At this time, the viscosity refers to a value measured by putting a sample at room temperature (25° C.) using a Brookfield RVDV-III viscometer spindle No. 52 and performing a stabilization work at a point in time when a torque value becomes 80%.

Hereinafter, a method for preparing a composition for forming a polyimide film according to an embodiment will be described in detail.

A method for preparing a composition for forming a polyimide film according to an embodiment includes (A) a step of preparing a polyimide precursor solution by dissolving a diamine compound in an organic solvent and then reacting a dianhydride with the diamine compound; and (B) a step of preparing the composition for forming a polyimide film by adjusting a solid content.

Specifically, the step (A) is a step of polymerizing a polyimide precursor by mixing the diamine and the dianhydride in an equivalent ratio of 1:0.9 to 1:1.1. In this case, a polymerization condition is not particularly limited, but it is more preferable that a polymerization reaction is performed under an inert gas atmosphere, and as an example, the polymerization reaction may be performed while a nitrogen or argon gas is refluxed in a reactor. In addition, the polymerization reaction may be performed at a reaction temperature of 10° C. to 50° C. or 20° C. to 40° C. and may be performed for a reaction time of 10 hours to 40 hours or 15 hours to 30 hours, but is not necessarily limited thereto.

In addition, in an embodiment, the step (A) may further include a step of adding an aromatic diacid dichloride. This step may be a step of simultaneously adding and polymerizing the diamine, the dianhydride and the aromatic diacid dichloride or a step of preparing an oligomer having an amine terminus by reacting the diamine and the aromatic diacid dichloride with each other and then reacting the oligomer with an additional diamine and dianhydride, but is not necessarily limited thereto. When the oligomer having the amine terminus is prepared and then reacted with the additional diamine and dianhydride, a block-type polyamideimide may be prepared, and a mechanical properties of the film may be further improved.

For example, when the oligomer having the amine terminus is prepared, the step (A) may include (A-1) a step of reacting the diamine with the aromatic diacid dichloride; (A-2) a step of purifying and drying the obtained oligomer; and (A-3) a step of reacting the purified oligomer, the diamine compound, and the dianhydride with each other to prepare the polyimide precursor solution. In this case, the diamine compound may be added in a molar ratio of 1.01 to 2 with respect to the aromatic diacid dichloride to prepare an amine-terminated polyamide oligomer. A molecular weight of the oligomer is not particularly limited, but may be, for example, a weight average molecular weight of 1,000 to 3,000 g/mol.

In addition, the step (B) may further include a step of imidizing the polyimide precursor prepared in the step (A). This step may be performed through chemical imidization, and the polyimide precursor further including any one or two or more selected from the group consisting of an imidization catalyst and a dehydrating agent may be imidized. The imidization catalyst may be any one or two or more selected from the group consisting of pyridine, isoquinoline and β-quinoline. In addition, the dehydrating agent may be any one or two or more selected from the group consisting of an acetic anhydride, a phthalic anhydride, a maleic anhydride, and the like, but is not necessarily limited thereto.

In an embodiment, when the chemical imidization is not performed as described above, the composition for forming a film according to an embodiment may not further include any one or two or more selected from the group consisting of the imidization catalyst and the dehydrating agent.

In this case, the step (B) may further include, the step of imidizing the polyimide precursor, a step of obtaining a solid (polyamideimide powder) by precipitating and purifying the imidized polyimide precursor in a solvent, and the composition for forming a polyimide film may be obtained by dissolving the solid in an organic solvent to adjust a solid content.

A molecular weight of the polyimide according to an embodiment is not particularly limited, but may be, for example, 50,000 to 1,000,000 g/mol, specifically 50,000 to 800,000 g/mol, and more specifically 50,000 to 500,000 g/mol.

In addition, an embodiment provides a polyimide film prepared by using the composition for forming a polyimide film.

The polyimide film according to an embodiment may have a low yellowness and an excellent transparency, a high modulus, and an excellent mechanical strength by including the structural unit derived from the diamine compound of the Formula 11.

The polyimide film according to an embodiment may have a thickness of 20 to 500 um, for example, 30 to 300 um, for example, 40 to 100 um.

In addition, the polyimide film according to an embodiment may have a modulus according to ASTM D882 of 6 GPa or more, 7 GPa or more, or 7.2 GPa or more.

In addition, the polyimide film according to an embodiment may have a YI according to ASTM E313 of 20 or less, 15 or less, or 10 or less, have a haze according to ASTM D1003 of 5.0 or less, 4.0 or less, or 3.0 or less, and have a total light transmittance according to ASTM D1003 of 80% or more, 85% or more, or 87% or more.

That is, the polyimide film according to an embodiment may implement an excellent mechanical strength while maintaining colorless properties even in a thickness range of 40 to 100 μm.

The polyimide film according to an embodiment may implement excellent optical properties and mechanical properties as described above by using a diamine compound having a specific structure as a monomer. Specifically, an embodiment may provide a polyimide film having optical properties, mechanical strength, and flexibility by including the structural unit derived from the diamine compound represented by the Formula 11. Accordingly, the polyimide film according to an embodiment may be applied to various fields such as a substrate for an element, a cover substrate for a display, an optical film, an integrated circuit (IC) package, an electrodeposition film, a multilayer flexible printed circuit (FPC), a tape, a touch panel, and a protective film for an optical disk.

Hereinafter, a method for preparing a polyimide film according to an embodiment will be described in detail.

The film according to an embodiment may be prepared by coating the composition for forming the polyimide film including the polymer and the solvent according to an embodiment on a substrate and then drying and/or stretching the composition.

Specifically, the film according to an embodiment may be prepared through chemical curing or thermal curing.

The chemical curing may include a step of preparing a polyimide-based resin by imidizing the polyimide precursor solution according to an embodiment; and a step of forming a film by coating a resin composition (composition for forming a polyimide film) in which the polyimide-based resin is dissolved in an organic solvent.

The imidization is the same as described above, and a description thereof will thus be omitted.

The step of forming the film is a step of forming the film by coating the composition for forming a film on the substrate and then drying the composition for forming a film through heat treatment. The substrate may be, for example, glass, stainless steel, or a film, and the coating may be performed by a die coater, an air knife, a reverse roll, a spray, a blade, casting, gravure, spin coating, or the like.

The heat treatment may be, for example, stepwise performed. For example, the heat treatment may be performed through stepwise heat treatment that primarily dries the composition for forming a film at 70° C. to 160° C. for 1 minute to 2 hours and secondarily dries the composition for forming a film at 150° C. to 350° C. for 1 minute to 2 hours. However, temperature and time conditions are not necessarily limited to the above temperature and time conditions, and for example, the primary drying may be performed at 80° C. to 150° C., 70° C. to 110° C., 130° C. to 150° C., 90° C., 120° C., or 140° C., for 10 minutes to 90 minutes, 10 minutes to 60 minutes, 20 minutes to 50 minutes, or 30 minutes, and the secondary drying may be performed at 200° C. to 300° C., 220° C. to 300° C., or 250° C. to 300° C. for 10 minutes to 90 minutes, 30 minutes to 90 minutes, or 40 minutes to 80 minutes. In this case, in the stepwise heat treatment, a temperature may be raised preferably in the range of 1 to 20° C./min during each step movement. In addition, the heat treatment may be performed in a separate vacuum oven or an oven filled with an inert gas, and the like, but is not necessarily limited thereto.

In addition, the thermal curing according to an embodiment may be performed at 100 to 450° C., 120 to 450° C., or 150 to 450° C. More specifically, the thermal curing may be performed at 80 to 100° C. for 1 minute to 2 hours, at 100 to 200° C. for 1 minute to 20 hours, or at 200 to 450° C. for 1 minute to 2 hours, and stepwise thermal curing may also be performed under two or more selected from these temperature conditions. In addition, the thermal curing may be performed in a separate vacuum oven or an oven filled with an inert gas, and the like, but is not necessarily limited thereto. In addition, if necessary, a drying step may be additionally performed before the thermal curing step. The drying step may be performed at a temperature of 50° C. to 150° C., 50° C. to 130° C., 60° C. to 100° C., or about 80° C., but is not necessarily limited thereto.

In addition, the polyimide film may be prepared by further mixing one or more additives selected from the group consisting of a flame retardant, an adhesion improver, an inorganic particle, an antioxidant, an ultraviolet inhibitor, a plasticizer, and the like, with the polyimide precursor solution.

In addition, the polyimide film according to an embodiment may be provided as a multilayer structure having two or more layers.

Specifically, the multilayer structure may further include a functional coating layer on the other surface of at least one of the polyimide film or the substrate, if necessary. Non-restrictive examples of the functional coating layer may include a hard coating layer, an anti-static layer, an anti-fingerprint layer, an anti-fouling layer, an anti-scratch layer, a low refractive layer, an anti-reflection layer, a shock-absorbing layer, and the like, and the multilayer structure may include at least one or two or more functional coating layers.

In an embodiment, various types of molded articles may be prepared by using the polyimide film. The polyimide film may be applied to a printed wiring board, a flexible circuit board, and the like, including a film, a protective film, or an insulating film as an example of the molded article, but is not limited thereto. Specifically, the polyimide film may be applied to a protective film that may substitute for a cover glass, and may be variously applied in various industrial fields including displays, which is an advantage.

More specifically, the polyimide film may be used as a window cover film of a flexible display or the like.

The polyimide film according to an embodiment includes the structural unit derived from the diamine compound represented by the Formula 11, and may thus implement excellent optical properties such as a high transparency and a low yellowness and an excellent modulus. Accordingly, the polyimide film according to an embodiment may be used as a window cover film of a flexible display panel or the like. A window cover including the polyimide film according to an embodiment may be used as a material substituting for tempered glass because it has more excellent optical properties to have excellent visibility and has a high modulus and an excellent mechanical strength.

Hereinafter, an embodiment will be described by way of example for a specific description of the present invention, but the present invention is not limited to the following embodiment.

In the following experiment, physical properties were measured as follows.

<Weight Average Molecular Weight>

A film was dissolved in a DMAc eluent containing 0.05M LiCl, and a weight average molecular weight is measured. For GPC, Waters GPC system, Waters 1515 isocratic HPLC Pump, and Waters 2414 Refractive Index detector were used, for a column, Olexis, Polypore, and mixed D columns were connected to each other, such that polymethyl methacrylate (PMMA STD) was used as a standard material, and analysis was performed at 35° C. and a flow rate of 1 mL/min.

<Modulus>

Based on an ASTM D882 standard, a module was measured using UTM 3365 available from Instron® under a condition in which a polyamideimide film having a length of 50 mm and a width of 10 mm was pulled at 50 mm/min at 25° C. A thickness of the film was measured and a measured value was input to an instrument. A modulus unit is GPa.

[Preparation Example 1] Preparation of Diamine Compound 1

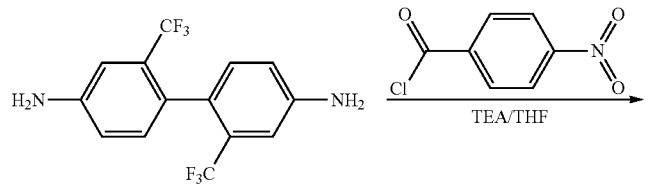

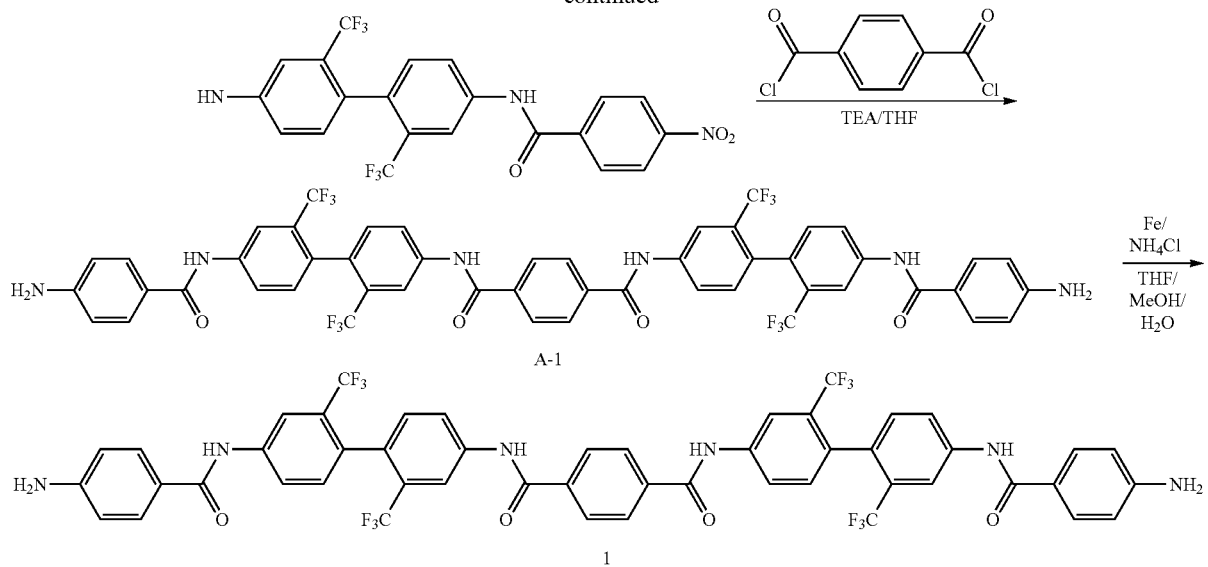

Preparation of Compound A 30 g of 2,2'-bis(trifluoromethyl)benzidine (TFMB) was dissolved in 300 ml of tetrahydrofuran (THF) in a reactor, and 14.22 g of triethylamine (TEA) was added at room temperature (25° C.). 17.3 g of 4-nitrobenzoyl chloride was dissolved in 150 ml of THF and added to the reaction solution, and a mixture was then stirred at room temperature for 4 hours. Then, 400 ml of ethyl acetate and 400 ml of distilled water were added to separate layers, and an aqueous layer was removed. An organic layer was washed once with 300 ml of distilled water, and then dried with magnesium sulfate and filtered. The organic layer was concentrated under reduced pressure and separated by column chromatography using hexane and EA to obtain Compound A (8.92 g)

$^1$H-NMR (DMSO-$d_6$, 500 MHz, ppm): 10.82 (s, 1H), 8.37~8.16 (m, 6H), 7.27 (d, 1H), 6.91 (m, 2H), 6.74 (d, 1H), 5.63 (s, 2H).

Preparation of Compound A-1

8.92 g of Compound A obtained above was dissolved in 160 ml of THF, 3.85 g of TEA was added at room temperature, 1.93 g of terephthaloyl chloride was added, and a mixture was then stirred at room temperature for 4 hours. Then, 150 ml of EA and 150 ml of distilled water were added to separate layers, and an aqueous layer was then removed. An organic layer was washed once with 150 ml of distilled water, and then dried with magnesium sulfate and filtered. The organic layer was concentrated under reduced pressure until a solid was precipitated, 150 ml of Hexane was added, and the resulting solid was filtered and dried to obtain Compound A-1 (9.88 g).

$^1$H-NMR (DMSO-$d_6$, 500 MHz, ppm): 10.90 (s, 2H), 10.77 (s, 2H), 8.37 (m, 8H), 8.18 (d, 4H), 8.08 (m, 8H), 7.38 (m, 4H).

Preparation of Diamine Compound 1

9.88 g of Compound A-1 obtained above was dissolved in 100 ml of THF, 50 ml of methanol (MeOH), and 50 ml of distilled water, and 7.22 g of Fe powder and 6.92 g of ammonium chloride (NH$_4$Cl) were added at room temperature. A temperature was raised to 60° C. and a mixture was stirred for 8 hours. A solid material present in a reaction solution was filtered using 200 ml of Celite and EA, 200 ml of distilled water was added to separate layers, and an aqueous layer was then removed. An organic layer was washed once with 150 ml of distilled water, and then dried with magnesium sulfate and filtered. The organic layer was concentrated under reduced pressure until a solid was precipitated, 100 ml of dichloromethane (DCM) and 100 ml of Hexane were sequentially added, and the resulting solid was filtered and dried to obtain Diamine Compound 1 (8.90 g).

$^1$H-NMR (DMSO-$d_6$, 500 MHz, ppm): 10.75 (s, 2H), 10.11 (s, 2H), 8.30 (s, 2H), 8.13 (s, 4H), 8.06 (dd, 4H), 7.72 (d, 4H), 7.32 (dd, 4H), 6.58 (d, 4H), 5.79 (s, 4H).

Example 1

Preparation of Composition for Forming Polyimide Film

In a reactor under a nitrogen atmosphere, 290 g of N,N-dimethylacetamide (DMAc) and 26 g of 2,2'-bis(trifluoromethyl)benzidine (TFMB) were added and sufficiently stirred, 11.8 g of terephthaloyldichloride (TPC) was added, and these materials were then stirred for 6 hours to be dissolved and reacted with each other. Then, a reaction product obtained by precipitation and filtration using an excessive amount of water was vacuum-dried at 90° C. for 6 hours or more to obtain 32 g of an oligomer.

Again, in the reactor under the nitrogen atmosphere, N,N-dimethylacetamide (DMAc), 9.9 g of the oligomer, and 3.1 g of the Diamine Compound 1 obtained in Preparation Example 1, and 1.3 g of additional 2,2'-bis(trifluoromethyl)-benzidine (TFMB) were added to make 100 mol of aromatic diamine, and cyclobutanetetracarboxylic dianhydride (CBDA) and 4,4'-hexafluoroisopropylidene diphthalic anhydride (6FDA) were sequentially added so that a molar ratio is a molar ratio as illustrated in the following Table 1 and were dissolved and reacted with each other while being stirred at 40° C. for 12 hours to prepare a polyimide precursor. In this case, the respective monomers were added in amounts as shown in a composition ratio of the following Table 1, a solid content was adjusted to be 10 wt %, and a temperature of the reactor was maintained at 40° C.

Then, pyridine and acetic anhydride were sequentially added to the polyimide precursor solution at 2.5 times the mole of a total content of dianhydride, respectively, and stirred at 60° C. for 12 hours to prepare a composition including a polyamideimide resin (Composition 1 for forming a polyimide film). A viscosity of the prepared composition was 40,000 cps, and a final solid content of the prepared composition was 9.1 wt %.

Preparation of Polyimide Film

Solution casting of the composition for forming a polyimide film of Example 1 was performed on a glass substrate using an applicator. Then, the composition for forming a polyimide film was primarily dried at 90° C. for 30 minutes using a convection oven, additionally heat-treated at 280° C. for 1 hour under a nitrogen stream condition, and then cooled at room temperature. Then, a film formed on the glass substrate was separated from the glass substrate to obtain a polyimide film of Example 1 having a thickness of about 50 μm.

Example 2

A composition for forming a polyimide film and a polyimide film having a thickness of about 50 μm were obtained in the same manner as in Example 1 except that a composition illustrated in the following Table 1 was used. A viscosity of the prepared composition was 31,000 cps, and a final solid content of the prepared composition was 9.1 wt %.

Comparative Example 1

A composition for forming a polyimide film and a polyimide film having a thickness of about 50 μm were obtained in the same manner as in Example 1 except that 100 mol of TFMB was used instead of the diamine compound in a molar ratio of TFMB:diamine compound 1=90:10 in Example 1 as shown in the following Table 1. A viscosity of the prepared composition was 31,000 cps, and a final solid content of the prepared composition was 9.0 wt %.

TABLE 1

| | Composition (molar ratio) | | | | | Modulus (GPa) |
|---|---|---|---|---|---|---|
| | TFMB | Diamine Compound 1 | TPC | 6FDA | CBDA | |
| Example 1 | 90 | 10 | 55 | 15 | 30 | 7.3 |
| Example 2 | 80 | 20 | 55 | 15 | 30 | 7.4 |
| Comparative Example 1 | 100 | — | 55 | 15 | 30 | 7.1 |

Referring to Table 1, it may be confirmed that the polyimide films according to Examples 1 and 2 include the structural unit derived from the novel diamine compound according to an embodiment, and accordingly, have a very high modulus of 7.0 GPa or more and have a higher modulus than the film polyimide film according to Comparative Example 1.

That is, it is possible to prepare the polyimide film having a high modulus and mechanical properties while maintaining excellent optical properties from the novel diamine compound according to an embodiment.

The polyimide film prepared by using the novel diamine compound according to an embodiment may simultaneously implement excellent mechanical properties and optical properties.

Specifically, the novel diamine compound according to an embodiment may have a structure having a unit capable of improving mechanical properties and a unit capable of decreasing an electron transfer complex (CTC) effect, and may more effectively improve a mechanical strength without deteriorating a yellowness and a transparency of the polyimide film.

In addition, the diamine compound according to an embodiment may have excellent solution handling properties to improve preparation processability.

That is, the diamine compound according to an embodiment may provide a polyimide film that is colorless and has a high modulus and an excellent mechanical strength, and has excellent preparation processability and may thus be applied to various industrial fields including displays.

The present invention has been described hereinabove by specific matters and exemplary embodiments, but these specific matters and exemplary embodiments have been provided only in order to assist in a more general understanding of the present invention. Therefore, the present invention is not limited to these exemplary embodiments, and various modifications and alterations may be made from this description by those skilled in the art to which the present invention pertains.

Therefore, the spirit of the present invention should not be limited to these exemplary embodiments, but the claims and all of modifications equal or equivalent to the claims are intended to fall within the scope and spirit of the present invention.

The invention claimed is:

1. A diamine compound represented by the following Formula 1:

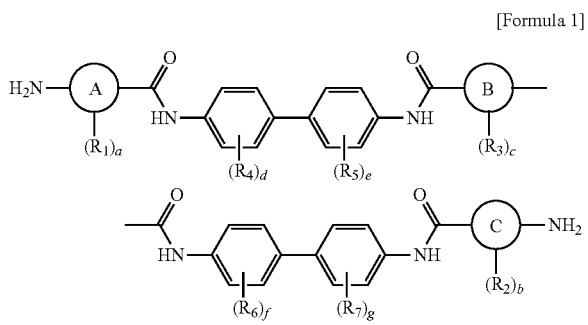

[Formula 1]

wherein rings A to C are each independently (C6-C20) aromatic rings;

$R_1$ to $R_3$ are each independently (C1-C10)alkyl, (C6-C20)aryl, (C3-C10)cycloalkyl, halo(C1-C10)alkyl, (C1-C10)alkylcarbonyl, (C1-C10)alkoxycarbonyl, (C6-C20)arylcarbonyl, —SiR$^a$R$^b$R$^c$, —NR$^d$R$^e$, —COOH, nitro, cyano, or halogen;

$R_4$ to $R_7$ are each independently (C1-C10)alkyl, (C6-C20)aryl, (C3-C10)cycloalkyl, halo(C1-C10)alkyl, (C1-C10)alkylcarbonyl, (C1-C10)alkoxycarbonyl, (C6-C20)arylcarbonyl, (C1-C10)alkoxy, —SiR$^a$R$^b$R$^c$, —NR$^d$R$^e$, —COOH, hydroxy, nitro, cyano, or halogen;

at least one of $R_4$ to $R_7$ is halo(C1-C10)alkyl, (C1-C10)alkylcarbonyl, (C1-C10)alkoxycarbonyl, (C6-C20)arylcarbonyl, —SiR$^a$R$^b$R$^c$, nitro, or cyano;

$R^a$ is (C1-C10)alkyl;

$R^b$ to $R^e$ are each independently hydrogen, (C1-C10)alkyl, or (C6-C20)aryl;

a to c are each independently an integer of 0 to 4; and d to g are each independently an integer of 1 to 4.

2. The diamine compound of claim 1, wherein the diamine compound represented by the Formula 1 is represented by the following Formula 2:

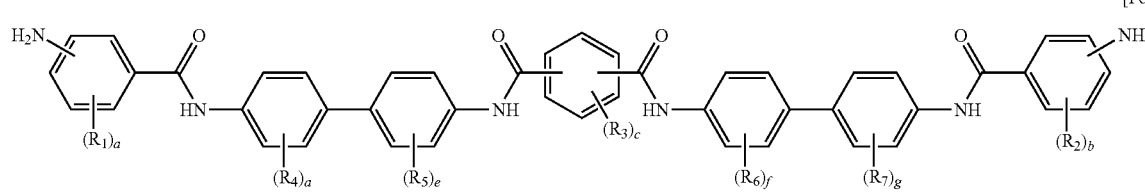

[Formula 2]

wherein $R_1$ to $R_3$ are each independently (C1-C7)alkyl, (C6-C12)aryl, (C3-C7)cycloalkyl, halo(C1-C7)alkyl, (C1-C7)alkylcarbonyl, (C6-C12)arylcarbonyl, —SiR$^a$R$^b$R$^c$, —NR$^d$R$^e$, —COOH, nitro, cyano, or halogen;

$R_4$ to $R_7$ are each independently (C1-C7)alkyl, (C6-C12)aryl, (C3-C7)cycloalkyl, halo(C1-C7)alkyl, (C1-C7)alkylcarbonyl, (C1-C7)alkoxycarbonyl, (C6-C12)arylcarbonyl, (C1-C7)alkoxy, —SiR$^a$R$^b$R$^c$, —NR$^d$R$^e$, —COOH, hydroxy, nitro, cyano, or halogen;

at least one of $R_4$ to $R_7$ is halo(C1-C7)alkyl, (C1-C7)alkylcarbonyl, (C1-C7)alkoxycarbonyl, (C6-C12)arylcarbonyl, —SiR$^a$R$^b$R$^c$, nitro, or cyano;

$R^a$ is (C1-C7)alkyl;

$R^b$ to $R^e$ are each independently hydrogen, (C1-C7)alkyl, or (C6-C12)aryl;

a to c are each independently an integer of 0 to 3; and d to g are each independently an integer of 1 to 3.

3. The diamine compound of claim 1, wherein the diamine compound represented by the Formula 1 is represented by the following Formula 3:

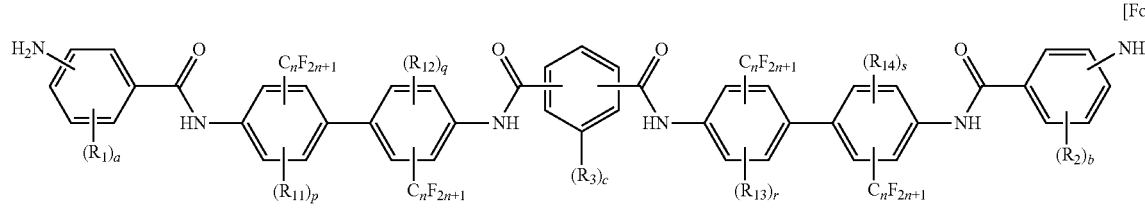

[Formula 3]

wherein
$R_1$ to $R_3$ and $R_{11}$ to $R_{14}$ are each independently halo(C1-C5)alkyl or halogen;
a to c are each independently 0 or 1;
p to s are each independently 0 or 1; and
n is an integer from 1 to 5.

4. The diamine compound of claim 1, wherein the diamine compound represented by the Formula 1 is represented by the following Formula 4:

[Formula 4]

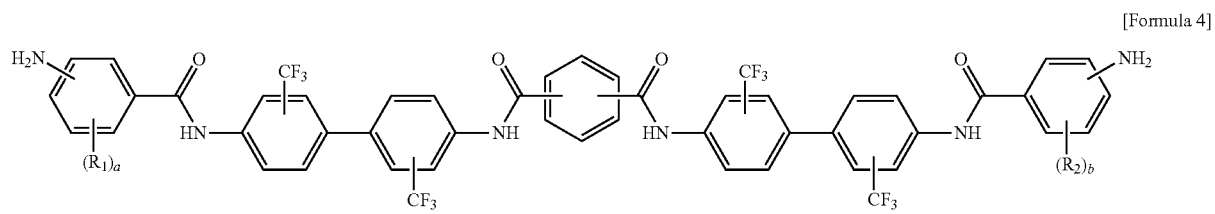

wherein
$R_1$ and $R_2$ are each independently halo(C1-C5)alkyl or halogen; and
a and b are each independently 0 or 1.

5. The diamine compound of claim 1, wherein the diamine compound represented by the Formula 1 is selected from the following:

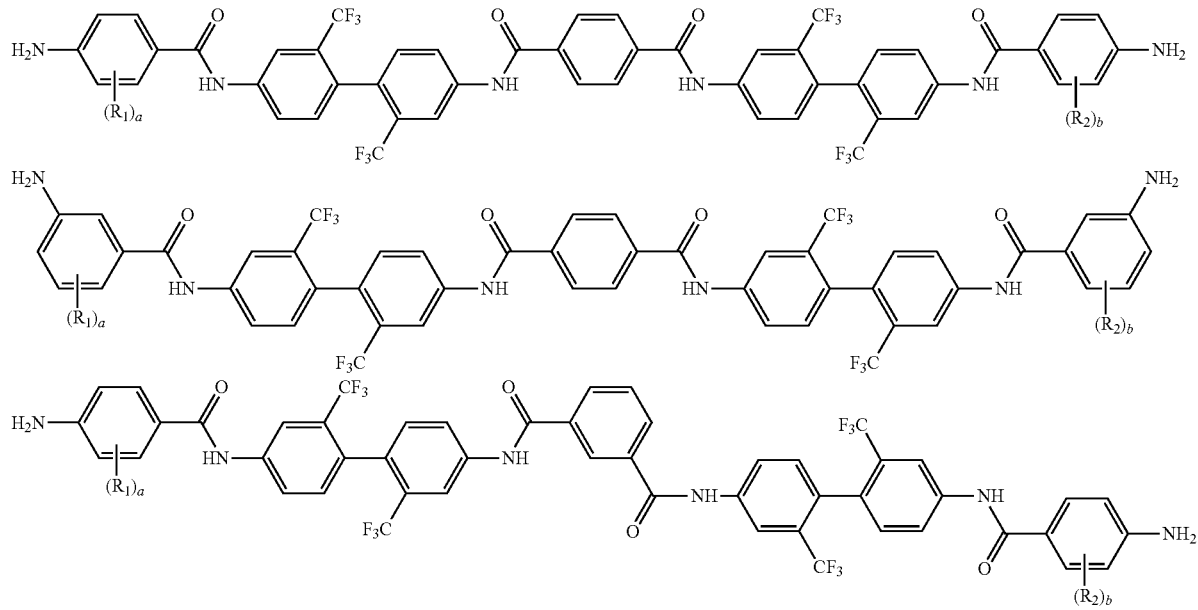

wherein $R_1$ and $R_2$ are each independently fluoro or trifluoromethyl; and
a and b are each independently 0 or 1.

* * * * *

UNITED STATES PATENT AND TRADEMARK OFFICE
CERTIFICATE OF CORRECTION

PATENT NO. : 12,180,144 B2  
APPLICATION NO. : 17/967096  
DATED : December 31, 2024  
INVENTOR(S) : Hyo Shin Kwak et al.

Page 1 of 1

It is certified that error appears in the above-identified patent and that said Letters Patent is hereby corrected as shown below:

In the Claims

Columns 43-44, Lines 14-31, Claim 2, delete:

"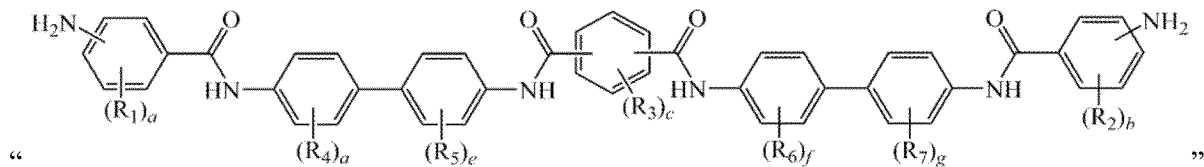"

And insert:

--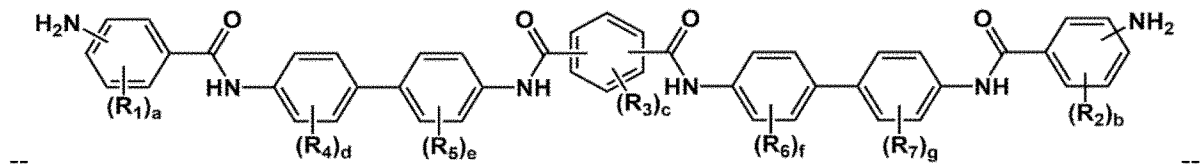--

Signed and Sealed this  
Eighth Day of April, 2025

Coke Morgan Stewart  
*Acting Director of the United States Patent and Trademark Office*